United States Patent [19]

Vogelstein et al.

[11] Patent Number: 5,955,263
[45] Date of Patent: Sep. 21, 1999

[54] SEQUENCE SPECIFIC DNA BINDING BY P53

[75] Inventors: Bert Vogelstein; Kenneth W. Kinzler, both of Baltimore, Md.; Michael I. Sherman, Glen Ridge, N.J.

[73] Assignees: Johns Hopkins University, Baltimore, Md.; Genzyme Corporation, Framingham, Mass.

[21] Appl. No.: 08/299,074

[22] Filed: Sep. 1, 1994

Related U.S. Application Data

[60] Division of application No. 07/860,758, Mar. 31, 1992, Pat. No. 5,362,623, which is a continuation-in-part of application No. 07/715,182, Jun. 14, 1991, abandoned.

[51] Int. Cl.$^6$ .......................... C12Q 1/68; G01N 33/574; G01N 33/48; C07H 21/02
[52] U.S. Cl. .............................. 435/6; 435/7.23; 436/63; 436/64; 536/23.1; 536/24.1
[58] Field of Search ........................... 435/6, 7.23, 7.92; 536/23.5, 23.1, 24.1; 436/63, 64

[56] References Cited

PUBLICATIONS

Kern et al., "Oncogenic Forms of p53 Inhibit p53–Regulated Gene Expressions", *Science* 256:827–830 (1992).
El–Deiry et al., "Definition of a Conseusus Binding Site for p53", *Nature Genetics* 1:45–49 (1992).
Bargonetti et al., "Wild–Type But Not Mutant p53 Immunopurified Proteins Bind to Sequences Adjacent to the SV40 Origin of Replication," *Cell* 65:1–9 (1991).
Jelinek et al., "Ubiquitous, Interspersed Repeated Sequences in Mammalian Genomes", *Proc. Natl. Acad. Sci. USA*, 77(3):1398–1402 (1980).
Mercer et al., "Negative Growth Regulation in a Glioblastoma Tumor Cell Line That Conditionally Expresses Human Wild–Type p53", *Proc. Natl. Acad. Sci. USA* 87:6166–6170 (1990).
Diller et al., "p53 Functions as a Cell Cycle Control Protein in Osteosarcomas", *Molecular and Cellular Biology* 10(11):5772–5781 (1990).
Baker et al., "Suppression of Human Colorectal Carcinoma Cell Growth by Wild–Type p53", *Science* 249:912–915 (1990).
Kern et al., "Mutant p53 Proteins Bind DNA Abnormally in vitro ", *Oncogene* 6(1):131–136 (1990).
Finlay et al., "The p53 Proto–Oncogene Can Act As a Suppressor of Transformation", *Cells* 57:1083–1093 (1989).
Romano et al., "Identification and Characterization of a p53 Gene Mutation in a Human Osteosarcoma Cell Line", *Oncogene* 4:1483–1488 (1989).
Yewdell et al., "Monoclonal Antibody Analysis of p53 Expression in Normal and Transformed Cells", *Journal of Virology* 59(2):444–452 (1986).
Nigro et al., "Mutations in the p53 Gene Occur in Diverse Human Tumor Types", *Nature* 342:705–708 (1989).
Eliyahu et al., "Wild–type p53 Can Inhibit Oncogene–Mediated Focus Formation", *Proc. Natl. Acad. Sci. USA* 86:8763–8767 (1989).
Weintraub et al., "Activation of Muscle–Specific Genes in Pigment, Nerve, Fat, Liver, and Fibroblast Cell Lines by Forced Expression of MyoD", *Proc. Natl. Acad. Sci. USA* 86:5434–5438 (1989).
Weintraub et al., "The MCK Enhancer Contains a p53 Responsive Element", *Proc. Natl. Acad. Sci. USA*, 88:4570–4571 (1991).
Zambetti et al., "Wild–type p53 Mediates Positive Regulation of Gene Expression Through a Specific DNA Sequence Element", *Genes & Development* 6:1143–1152 (1992).
Baker et al., "Chromosome 17 Deletions and p53 Gene Mutations in Colorectal Carcinomas", *Science*, 244:217–221 (1989).

*Primary Examiner*—Sheela Huff
*Assistant Examiner*—Yvonne Eyler
*Attorney, Agent, or Firm*—Banner & Witcoff, Ltd.

[57] ABSTRACT

Specific sequences in the human genome are the sites of strong binding of wild-type p53 protein, but not mutant forms of the protein. These sequences are used diagnostically to detect cells in which the amount of wild-type p53 is diminished. The sequences can also be used to screen for agents which correct for loss of wild-type p53 to DNA in cancer cells.

24 Claims, 28 Drawing Sheets

FIG. 3A

```
         10        20        30        40        50        60        70        80        90
AATACGACTCACTATAGGGCGAATTGGGCTACCGGGCCCCCTCGAGGTCGACGGTATCGATAAGCTTGATATTCTCCCAGATGTAGTG
TTATGCTGAGTGATATCCCGCTTAACCCGATGGCCCGGGGGAGCTCCAGCTGCCATAGCTATTCGAACTATAAGAGGGTCTACATCAC
                                                              ←――――――
                                                                VECTOR 78

100       110       120       130       140       150       160       170       180
AAAGCAGGTAGATTGCCTGCCTGGACTTGCCTTGCCCTTTCTCTTTATTACTTCTCTTTTCTCTTCT
TTTCGTCCATCTAACGGACGGACCTGAACGGAAACGGGAAAGAGAAATAATGAAAGAAGAAAAGAAGAGA 190       200       210       220       230       240       250       260       270
TCTTCTTCTTCTTCTTCTTCTTCTTCTTCTTCTTCTTTTTTTGAGACAGAGTTTCACTCTTGTTGCCCAGGC
AGAAGAAGAAGAAGAAGAAGAAGAAGAAGAAGAAGAAAAAAACTCTGTCTCAAAGTGAGAACAACGGGTCCG 280       290       300       310       320       330       340       350       360
TAGAGGGCAATGGCGCAATCTCGGCTCACCGCAACCCTCCGCCTCCCAGGTTCAAGCGATTGGGGGATCCACTAGTTCTAGAGCGGCCGCC
ATCTCCCGTTACCGCGTTAGAGCCGAGTGGCGTTGGGAGGCGGAGGGTCCAAGTTCGCTAACCCCCTAGGTGATCAAGATCTCGCCGGCGG
                                                 ――――――→
                                                  VECTOR 370       380       390       400       410       420
ACCGGCGGTGGAGCTCGAGGTCGAAATCACAAGCTTTTGTTCCCTTTAGTGAGGGTTAAT
TGGCGCCACCTCGAGCTCCAGCTTTAGTGTTCGAAAACAAGGGAAATCACTCCCAATTA
```

FIG. 3B

```
        10         20         30         40         50         60         70         80         90
VECTOR→
AAGCTTGATAATCATGGAAGGTGAGTTTTTCCAGTGCTGTTCTCATGATAGTGACTAAGTCTCCCATGATCTGATGGTTTATAAAGGGCA
TTCGAACTATTAGTACCTCCACTCAAAAAGGTCACGACAAGAGTACTATCACTGATTCAGAGACTACCAAATATTTCCCGT 100        110        120        130        140        150        160        170        180
GTCCTTCTACACATGCTCTTGCTTGCTACCATGTAAGACATGTCCTGTGCTCCTCTCTTTTGCCTTCTGCCATGATTGTGAGACCTCCCCA
CAGGAAGATGTGTACGAGAACGATGGTACATTCTGTACGGACACGGAGGAGAAACGGAGACGGTACTAACACTCTGGAGGGGT
                  VECTOR→

190        200        210        220        230
GCCATGTGGAACTGTGAGTATCGAATTCCTGCAGCCCGGGGGGATCCACTAGTTCTAGA
CGGTACACCTTGACACTCATAGCTTAAGGACGTCGGGCCCCCTAGGTGATCAAGATCT
```

FIG. 8B
```
    1     2     3     4     5     6
  C B   C B   C B   C B   C B   C B
```
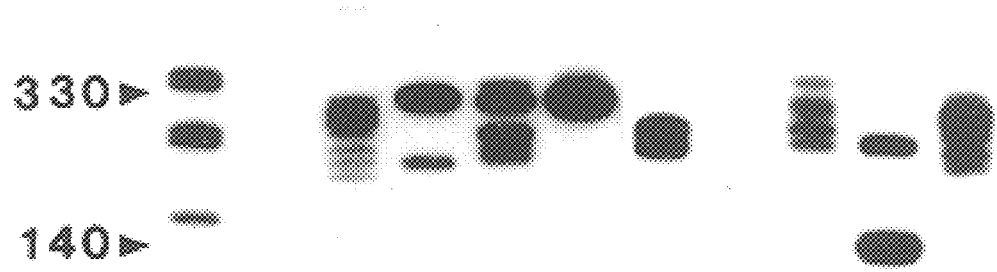
330▶
140▶
```
    7     8     9    10    11    12
  C B   C B   C B   C B   C B   C B
```
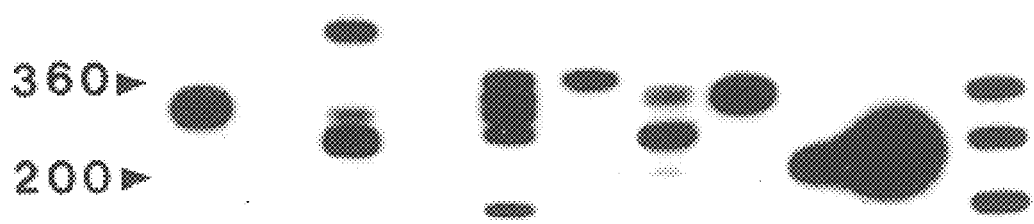
360▶
200▶

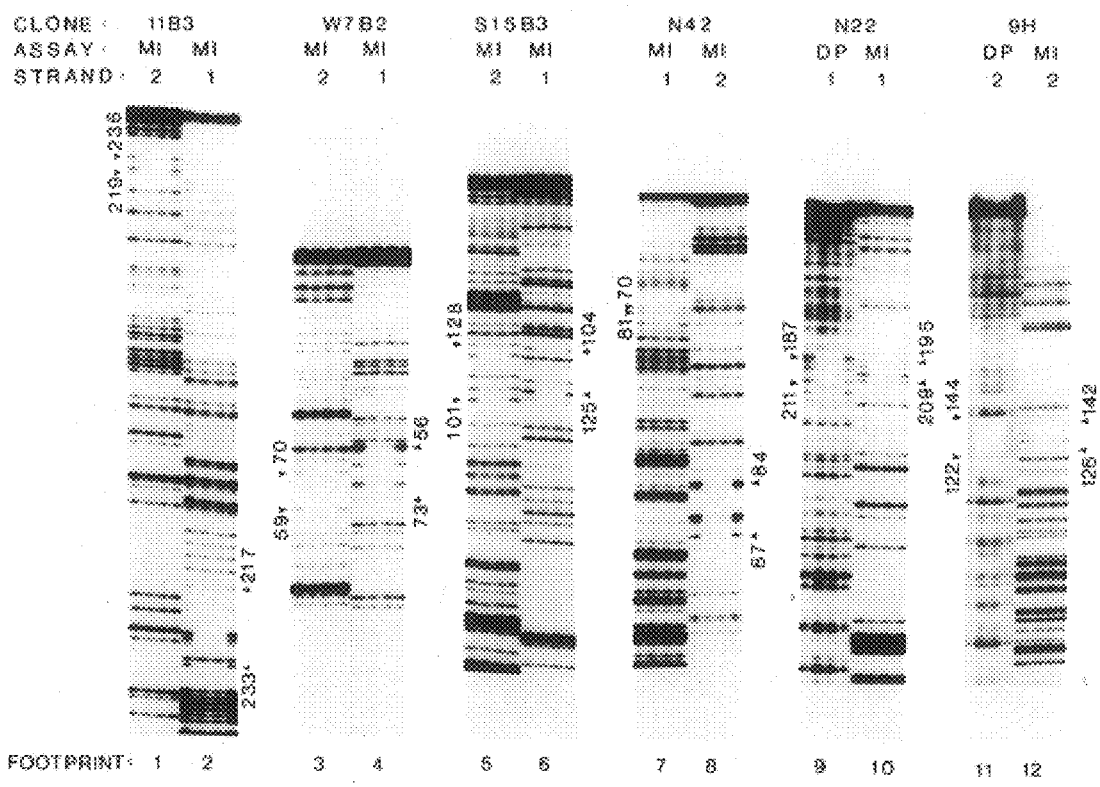

FIG. 10A

| Clone | Size (bp) | 5'-bp | nnnnnnnnnnn | R R R C W W G Y Y Y | nnnnnnnn |
|---|---|---|---|---|---|
| 1. S57 | 295 | 144 | cgacctgtcacacg | G G G C C T G T C a | |
| 2. N22 | 357 | 178 | attttcaccatgctt | c t G C A T G T C T | |
| 3. 11A2 | 387 | 317 | cccatcctccactg | A A C A a T G C C C | |
| 4. W211 | 249 | 119 | tttgtcctaccatcc | A G G C A T G C C T | |
| 5. W7B2 | 139 | 41 | tatctgtgcagctgt | G G G C A T G T T T | t |
| 6. 3H | 126 | 50 | aactagatcctttc | A G A C A T G T T a | |
| 7. 8A | 483 | 445 | gctggtgcacaagag | t G A C A T G T C C | |
| 8. 532 | 335 | 229 | catcatgccacctgc | A G G C A T G T T C | tggat |
| 9. 64A2 | 349 | 120 | caaaccagggtgtct | t G A C T T G C C T | atcctggggaggt |
| 10. W7A1 | 264 | 124 | gccaaacataaccac | c A G C T T G C C a | |
| 11. S61 | 202 | 1 | c | c C A A C T T G T C T | atctgtgttgat |
| 12. 11B3 | 248 | 201 | actgttgatgatgaa | A G A A A G C C C T | a |
| 13. N42 | 248 | 49 | gcagtgtggtggagg | A A A C A A G C C C | a |
| 14. S201 | 326 | 164 | tgttcatacctgtcc | A C A C T T G T C T | |
| 15. S15B3 | 248 | 83 | cttaattcagttgt | A A A C A T GaC T T | |
| 16. S592I | 254 | 39 | ctcagttctcagctg | G G A C T T G C C C | gttcattata |
| 17. S592II | 254 | 130 | tgcctcagcaccttc | A G G t TcT G C C | |
| 18. 2Nb | 470 | 42 | gcctttgttgtgccc | t G A C T T G C C C | |
| 19. 9H | 467 | 108 | gtattctcttttcct | A A G C A T G C C T | |
| 20. CBE10d | 425 | 89 | tgaaagcaggtagat | t G C C T T G C C T | |

Combined Nucleotide Usage (%) within the Two Monomers of the Consensus Binding Site:

FIG. 10B

| R | R | R | C | W | G | Y | Y | Y | nnnnnnnnnnn | 3'-bp |
|---|---|---|---|---|---|---|---|---|---|---|
| c | A | G | C | A | T | Ga | C | C | T | acctgtcacaccggg | 194 |
| A | G | G | C | A | A | G | T | C | a | cctctccactggcc | 227 |
| A | G | A | C | T | T | G | T | C | T | ctccggcctgaatga | 367 |
| | | | T | T | G | C | C | T | T | cactcgttattcct | 164 |
| A | G | G | C | A | A | G | C | T | T | cctgtgctagttccc | 91 |
| t | A | A | C | A | A | G | T | C | a | gtacaagtttatttt | 99 |
| c | G | G | A | C | g | T | G | T | T | tgtc | 483 |
| G | G | G | A | C | A | T | G | T | C | tgtgcttttgttgttt | 282 |
| t | A | G | G | A | C | A | T | T | C | ctccccctcccctc | 181 |
| A | G | G | G | C | A | g | T | G | C | taccacgctcagccc | 173 |
| G | G | G | A | C | C | A | T | G | T | T | ccgttttttggctatt | 49 |
| A | t | G | G | A | C | A | C | C | T | C | tgggggtgggg | 248 |
| t | t | G | G | A | C | C | T | T | C | agggcaggctgggac | 99 |
| A | G | G | A | C | C | A | T | G | T | T | acacctgtcttgttt | 214 |
| t | G | G | A | C | C | A | G | C | C | aattacaattcgatt | 143 |
| A | G | A | C | C | A | T | T | T | C | tggggtcactgctgc | 88 |
| t | G | A | C | C | T | T | G | T | T | cttcctttcagcat | 179 |
| A | G | A | C | A | T | T | T | G | T | gggaatgtcttgtgc | 91 |
| G | G | A | C | T | T | G | T | T | C | tttcatctcctctga | 157 |
| G | G | A | C | T | T | G | C | C | T | ggccttgcctttcct | 138 |

FIG. 10

| FIG. 10A | FIG. 10B |
|---|---|
| FIG. 10C | FIG. 10D |

FIG. 10C

| | 5'- R | R | R | R | C | W | W |
|---|---|---|---|---|---|---|---|
| A | 40 | 20 | 55 | 0 | | 53 | 15 |
| C | 13 | 3 | 3 | 93 | | 8 | 0 |
| G | 23 | 70 | 40 | 0 | | 8 | 3 |
| T | 23 | 5 | 0 | 5 | | 30 | 82 |

Synthetic Oligonucleotides:

| No. | | p53 Binding |
|---|---|---|
| 1. | AGGaATtCCT tgcaggaattcgat | - |
| 2. | AGGaATtCCT tgcaggaattcgat | - |
| 3. | AGGCATGTCT tgcaggaattcgat | - |
| 4. | AGGCATGCCT tgcaggaattcgat | + |
| 5. | AGGCAAGgCa tgcaggaattcgat | - |
| 6. | AGGCATGTCT tgcaggaattcgat | + |
| 7. | AGACATGCCT tgcaggaattcgat | + |
| 8. | AGGCATGTCT tgcaggaattcgat | + |
| 9. | AGGCATGCCT tgcaggaattcgat | - |
| 10. | AGGCATGTCT tgcaggaattcgat | - |

FIG. 10D

|   | G | Y | Y | Y | Y-3' |   |
|---|---|---|---|---|---|---|
| A | 0 | 0 | 0 | 12 |   | A |
| C | 0 | 50 | 68 | 35 |   | C |
| G | 100 | 0 | 0 | 3 |   | G |
| T | 0 | 50 | 30 | 48 |   | T |

```
A G G a A T t C C T
A G G C A T G C C T    atcaagcttatcgat
A G G C A A G C a      atcaagcttatcgat
A G G C A T G T C T    atcaagcttatcgat
A G A C A T G C C T    atcaagcttatcgat
A G G C A T G T C T    atcaagcttatcgat
```

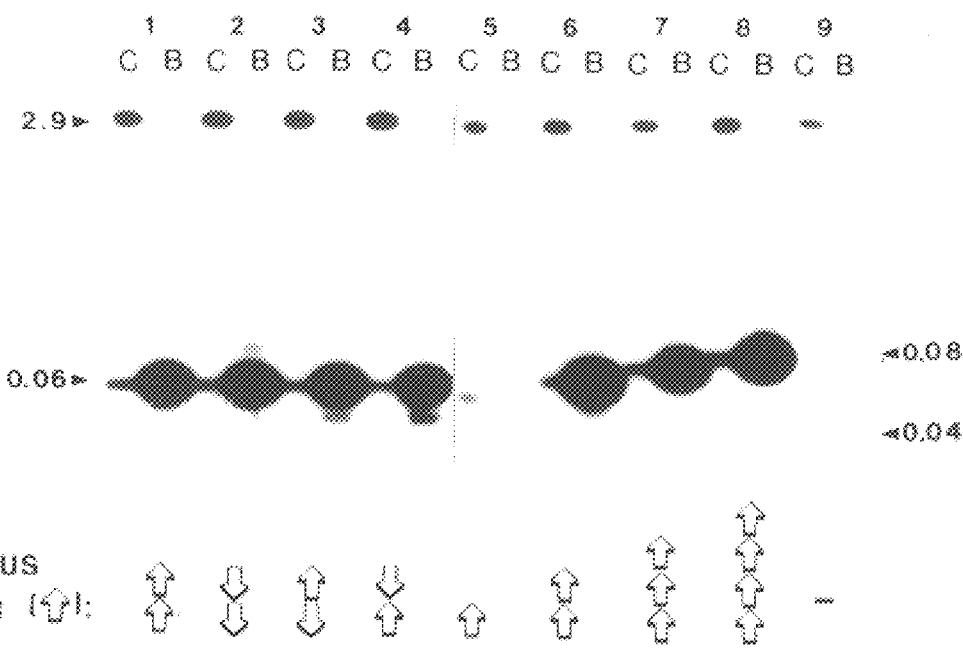

FIG. IIB p53:         w.t. 143 175 248 273 w.t.
       C     B    B   B   B   B   B 2.9 ▶    ——

0.06 ▶        ●                     ●

1    2    3   4   5   6   7

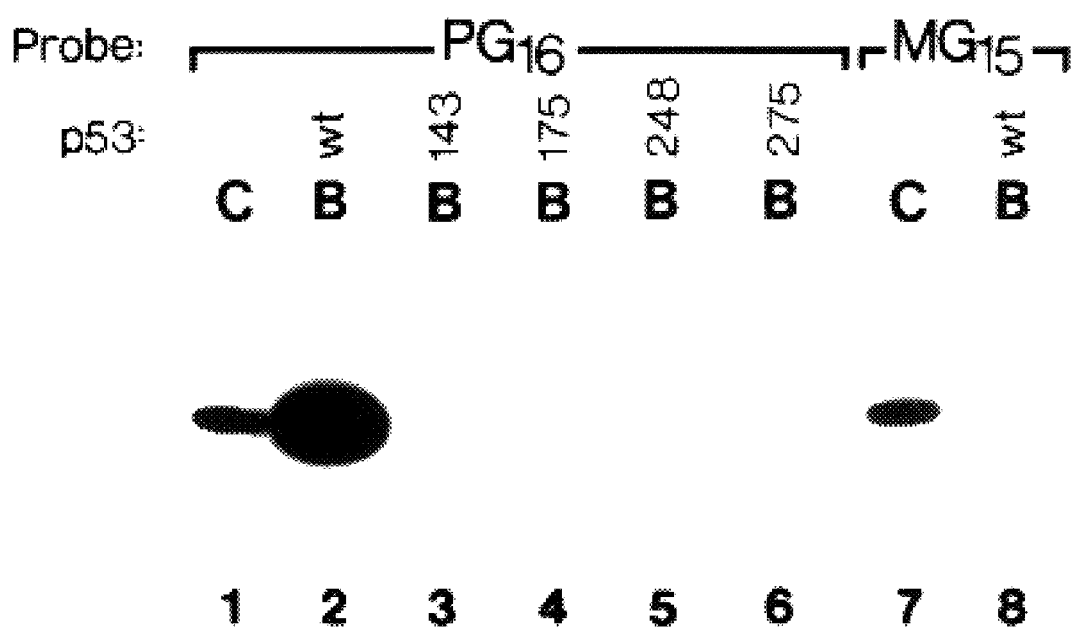

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
       (A) LENGTH: 405 base pairs
       (B) TYPE: nucleic acid
       (C) STRANDEDNESS: single
       (D) TOPOLOGY: linear (xi) SEQUENCE DESCRIPTION: SEQ ID NO:1:

```
AATACGACTC ACTATAGGGC GAATTGGGTA CCGGGCCCCC CCTCGAGGTC GACGGTATCG    60

ATAAGCTTGA TATTCTCCCC AGATGTAGTG AAAGCAGGTA GATTGCCTTG CCTGGACTTG   120

CCTGGCCTTG CCTTTTCTTT CTTTCTTTCT TTCTTTATTA CTTTCTCTTT TTCTTCTTCT   180

TCTTCTTCTT CTTCTTCTTC TTCTTCTTCT TCTTCTTCTT CTTCTTCTTC TTTTTTTTTT   240

GAGACAGAGT TTCACTCTTG TTGCCCAGGC TAGAGGGCAA TGGCGCGATC TCGGCTCACC   300

GCACCCTCCG CCTCCCAGGT TCAAGCGATT GGGGGATCCA CTAGTTCTAG AGCGGCCGCC   360

ACCGCGGTGG AGCTCCAGCT TTTGTTCCCT TTAGTGAGGG TTAAT                   405
```

(2) INFORMATION FOR SEQ ID NO:2:

(i) SEQUENCE CHARACTERISTICS:
       (A) LENGTH: 238 base pairs
       (B) TYPE: nucleic acid
       (C) STRANDEDNESS: single
       (D) TOPOLOGY: linear (xi) SEQUENCE DESCRIPTION: SEQ ID NO:2:

```
AAGCTTGATA ATCATGGAGG TGAGTTTTTC CAGTGCTGTT CTCATGATAG TGACTAAGTC    60

TCCCATGATC TGATGGTTTT ATAAAGGGCA GTCCTTCTAC ACATGCTCTC TTGCTTGCTA   120

CCATGTAAGA CATGCCTGTG CTCCTCTTTT GCCTTCTGCC ATGATTGTGA GACCTCCCCA   180

GCCATGTGGA ACTGTGAGTA TCGAATTCCT GCAGCCCGGG GGATCCACTA GTTCTAGA    238
```

(2) INFORMATION FOR SEQ ID NO:3:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:3:

```
RRRCWWGYYY                                                           10
```

(2) INFORMATION FOR SEQ ID NO:4:

(i) SEQUENCE CHARACTERISTICS:
       (A) LENGTH: 51 base pairs
       (B) TYPE: nucleic acid
       (C) STRANDEDNESS: single
       (D) TOPOLOGY: linear (xi) SEQUENCE DESCRIPTION: SEQ ID NO:4:

CGACCTGTCA CACCGGGGCC TGTCACAGCA TGACCTACCT GTCACACCGG G        51

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:5:

ATTTTCACCA TGCTTCTGCA TGTCTAGGCA AGTCACCTTC TCCACTGGCC        50

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:6:

CCCCATCCTC CACTGAAACA ATGCCCAGAC TTGTCTCTCC GGCCTGAATG A        51

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:7:

TTTGTCCTAC CATCCAGGCA TGCCTTTGCC TCACTCGTTA TTTCCT        46

(2) INFORMATION FOR SEQ ID NO:8:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:8:

TATCTGTGCA GCTGTGGGCA TGTTTTAGGC AAGCTTCCTG TGCTAGTTCC C        51

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:9:

AACTAGATCC TTTTCAGACA TGTTATAACA AGTCAGTACA AGTTTATTTT        50

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:10:

GCTGGTGCAC AAGAGTGACA TGTCCCGACG TGTTTTGTC        39

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:11:

```
CATCATGCCA CCTGCAGGCA TGTTCTGGAT GGGCTGTCTT GTGCTTTGTT GTTT          54
```

(2) INFORMATION FOR SEQ ID NO:12:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:12:

```
CAAACCAGGG TGTCTTGACT TGCCTATCCT GGGAGGTTGA CATGTTCCTC CCCTTCCCCC    60
TC                                                                  62
```

(2) INFORMATION FOR SEQ ID NO:13:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:13:

```
GCCAAACATA ACCACCAGCT GCCAAGGCAT GCAGTACCAC GCTCAGCCC               49
```

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:14:

```
CCAACTTGTC TATTCTGTGT TGATGGACAT GTTCCCGTTT TTGGCTATT                49
```

(2) INFORMATION FOR SEQ ID NO:15:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:15:

```
GCAGTGTGGT GGAGGAAACA AGCCCAGGAT GTGCCCAGGG CAGGCTGGGA C             51
```

(2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:16:

```
ACTGTTGATG ATGAAAGACA AGCCTAGGGC AGGTCCTGGG GGGTGGGG                 48
```

(2) INFORMATION FOR SEQ ID NO:17:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:17:

```
TGTTCATACC TGTCCACACT TGTCTATACC TGCCTACACC TGTCTTGTTT            50
```

(2) INFORMATION FOR SEQ ID NO:18:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:18:

```
CTTTAATTCA GTTGTAAACA TGACTTGTTC ATTATATGAC ATGTTCAATT ACAATTCGAT  60
T                                                                 61
```

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:19:

```
CTCAGTTCTC AGCTGGGACT TGCCCTGGCC AGCCCTGGGG TCACTGCTGC            50
```

(2) INFORMATION FOR SEQ ID NO:20:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:20:

```
TGCCTCAGCA CCTTCAGGTT CTGCCGGGCT TGTTCCTTTC CTTTCAGCAT            50
```

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:21:

```
GCCTTTGTTG TGCCCTGACT TGCCCAGACA TGTTTGGGAA TGTCTTGTGC            50
```

(2) INFORMATION FOR SEQ ID NO:22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:22:

```
GTATTCTCTT TTCCTAAGCA TGCCTTGACT TGTTCTTTCA TCTCCTCTGA            50
```

(2) INFORMATION FOR SEQ ID NO:23:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:23:

TGAAAGCAGG TAGATTGCCT TGCCTGGACT TGCCTGGCCT TGCCTTTTCT                50

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:24:

AGGAATTCCT                                                            10

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

AGGAATTCCT AGGAATTCCT                                                 20

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:26:

AGGCATGTCT                                                            10

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

AGGCATGCCT AGGCATGCCT                                                 20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

AGGCAAGGCA AGGCAAGGCA                                                 20

(2) INFORMATION FOR SEQ ID NO:29:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:29:

```
TGCAGGAATT CGATAGGCAT GTCTAGGCAT GTCTATCAAG CTTATCGAT           49
```

(2) INFORMATION FOR SEQ ID NO:30:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:30:

```
TGCAGGAATT CGATAGGCAT GTCTAGACAT GCCTATCAAG CTTATCGAT           49
```

(2) INFORMATION FOR SEQ ID NO:31:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:31:

```
TGCAGGAATT CGATAGACAT GCCTAGGCAT GTCTATCAAG CTTATCGAT           49
```

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:32:

```
TGCAGGAATT CGATAGGCAT GTCTATCAAG CTTATCGAT                      39
```

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:33:

```
TGCAGGAATT CGATATCAAG CTTATCGAT                                 29
```

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:34:

```
GAAAGAAAAG GCAAGGCCAG GAAAGT                                    26
```

(2) INFORMATION FOR SEQ ID NO:35:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (xi) SEQUENCE DESCRIPTION: SEQ ID NO:35:

GAAAGAAAAG GCAAGGCCAT TAAAGT                                    26

(2) INFORMATION FOR SEQ ID NO:36:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (xi) SEQUENCE DESCRIPTION: SEQ ID NO:36:

TGCCT                                                                       5

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:37:

GAGTAGAATT CTAATATCTC                                        20

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:38:

AGGCATGTCT                                                10

(2) INFORMATION FOR SEQ ID NO:39:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (xi) SEQUENCE DESCRIPTION: SEQ ID NO:39:

RRRCW                                                                   5

(2) INFORMATION FOR SEQ ID NO:40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:40:

CCTGCCTGGA CTTGCCTGG                                        19

(2) INFORMATION FOR SEQ ID NO:41:

(i) SEQUENCE CHARACTERISTICS:
        (A) LENGTH: 19 base pairs

```
        (B) TYPE: nucleic acid
        (C) STRANDEDNESS: single
        (D) TOPOLOGY: linear (xi) SEQUENCE DESCRIPTION: SEQ ID NO:41:

CCTTAATGGA CTTTAATGG                                                        19
```

SEQUENCE SPECIFIC DNA BINDING BY P53

This application is a division of application Ser. No. 07/860,758, filed Mar. 31, 1992 now issued as U.S. Pat. No. 5,362,623, which is a continuation-in-part of application Ser. No. 07/715,182, filed Jun. 14, 1991 now abandoned.

This work was partially supported by the U.S. government under NIH grants CA06973, CA09243, CA35494, CA09071 and CA43460. The U.S. government retains certain rights in this invention.

TECHNICAL FIELD OF THE INVENTION

This invention relates to diagnostic and therapeutic methods for detecting and alleviating cancers. Specifically it relates to the identification of DNA sequences specifically bound by tumor suppressor p53.

BACKGROUND OF THE INVENTION

The gene for the nuclear phosphoprotein p53 is the most commonly mutated gene yet identified in human cancers (Vogelstein, B., *Nature,* 348:681 (1990)). Missense mutations occur in tumors of the colon, lung, breast, ovary, bladder, and several other organs (S. J. Baker, et al., *Science,* 244:217 (1989); J. M. Nigro, et al., *Nature,* 342:705 (1989); T. Takahashi, et al., *Science,* 246:491 (1989); Romano, et al., *Oncogene,* 4:1483 (1989), Menon, *Proc. Natl Acad. Sci. USA,* 87:5435 (1990); Iggo, et al., *Lancet ii,* 675 (1990); T. Takahashi, et al., *J. Clin. Invest.* 86:363 (1990); Mulligan, *Proc. Natl Acad. Sci. USA,* 87:5863 (1990); Bartek, et al., *Oncogene,* 5:893 (1990); Stratton et al., *Oncogene,* 5:1297 (1990)). One of the important challenges of current cancer research is the elucidation of the biochemical properties of the p53 gene product and the way in which mutations of the p53 gene effect these properties.

Although some biological characteristics of p53 have been defined, such as its ability to suppress the growth of in vitro transformed murine cells (Eliyahu, et al., *Proc. Natl Acad. Sci. USA* 86:8763 (1989); Finlay, et al., *Cell,* 57:1083 (1989)) or human cancer cells (Baker, et al., *Science,* 249:912 (1990); Mercer, et al., *Proc. Natl Acad. Sci,* USA, 87:6166 (1990); Diller et al., *Mol. Cell Biol.* 10:5772 (1990)), the biochemical basis of this suppression remains largely unknown. As a step towards understanding such properties, we have attempted to determine whether p53 binds to specific DNA sequences within the human genome.

SUMMARY OF THE INVENTION

It is an object of the invention to provide a method for detecting the presence of wild-type p53 protein in a cell.

It is another object of the invention to provide a method for providing the physiological effect of wild-type p53 protein to a cell.

It is yet another object of the invention to provide a double-stranded DNA fragment which contains a p53-specific DNA binding site.

It is yet another object of the invention to provide a single-stranded oligonucleotide or oligonucleotide containing nucleotide analogs which can specifically complex to a p53-specific DNA binding site.

It is still another object of the invention to provide methods for identifying compounds which specifically bind to p53-specific DNA binding sequences.

It is still another object of the invention to provide methods for identifying compounds which restore the ability of mutant p53 proteins to bind to specific DNA binding sequences.

These and other objects of the invention are provided by one or more of the embodiments described below. In one embodiment a method is provided for detecting the presence of wild-type p53 protein in a cell, comprising the steps of: contacting a p53-specific binding DNA fragment with a cell lysate from a tissue of a human to bind the DNA fragment to wild-type p53 present in the cell lysate; and detecting the binding of the p53-specific-binding DNA fragment to wild-type p53.

In another embodiment of the invention a method is disclosed for providing the physiological effect of wild-type p53 protein to cell, comprising the steps of: providing to a cell a compound which is able to specifically complex with a p53-specific binding site.

In yet another embodiment a double-stranded DNA fragment is provided which comprises a p53-specific-DNA binding site, wherein the fragment comprises more than one monomer repeat of the sequence 5'-RRRCWWGYYY-3' (SEQ ID NO:3) and wherein the fragment is covalently attached to an insoluble polymeric support.

In another embodiment of the invention a single-stranded oligonucleotide containing natural nucleotides and/or nucleotide analogs is provided which is able to complex specifically with a p53-specific binding site, said binding site comprising more than one monomer of the sequence 5'-RRRCWWGYYY-3' (SEQ ID NO:3).

In yet another embodiment of the invention a method is provided for identifying compounds which specifically bind to p53-specific DNA binding sequences, comprising the steps of: contacting a p53-specific DNA binding fragment immobilized on a solid support with a test compound to bind the test compound to the DNA fragment; and determining the amount of test compound which is bound to the DNA fragment.

In even another embodiment of the invention a method is provided for identifying compounds which specifically bind to p53-specific-DNA binding sequences, comprising the steps of: contacting a p53-binding DNA fragment immobilized on a solid support with both a test compound and wild-type p53 protein to bind the wild-type p53 protein to the DNA fragment; determining the amount of wild-type p53 protein which is bound to the DNA fragment, inhibition of binding of wild-type p53 protein by the test compound suggesting binding of the test compound to the p53-specific DNA binding sequences.

In still another embodiment a method of prescreening agents for use in cancer therapy is provided comprising: measuring the amount of binding of a p53 protein which is encoded by a mutant gene found in cancer cells of a patient to a DNA molecule which comprises more than one monomer of RRRCWWGYYY (SEQ ID NO:28); measuring the amount of binding of said p53 protein to said DNA molecule in the presence of a test substance; and comparing the amount of binding of the p53 protein in the presence of said test substance to the amount of binding of the p53 protein in the absence of said test substance, a test substance which increases the amount of binding being a candidate for use in cancer therapy.

In another embodiment of the invention a method is provided for prescreening agents for use in cancer therapy comprising: contacting a transfected cell with a test substance, said transfected cell containing a p53 protein which is encoded by a mutant gene found in cancer cells of a patient and a reporter gene construct comprising a reporter gene which encodes an assayable product and a sequence which conforms to the p53 consensus binding site having more than one monomer of RRRCWWGYYY (SEQ ID NO:3), wherein said sequence is upstream from and adjacent to said reporter gene; and determining whether the amount of expression of said reporter gene is altered by the test substance, a test substance which alters the amount of expression of said reporter gene being a candidate for use in cancer therapy.

In still another embodiment a method of prescreening agents for use in cancer therapy is provided comprising: adding RNA polymerase and ribonucleotides to a transcription construct, said transcription construct comprising a reporter gene which encodes an assayable product and a sequence which conforms to the p53 consensus binding site having more than one monomer of RRRCWWGYYY (SEQ ID NO:3), said sequence being upstream from and adjacent to said reporter gene, said step of adding being effected in the presence and absence of a test substance; determining whether the amount of transcription of said reporter gene is altered by the presence of said test substance, a test substance which alters the amount of transcription of said reporter gene being a candidate for use in cancer therapy.

In a further embodiment a DNA construct is provided comprising: a reporter gene which encodes an assayable product; and a sequence which conforms to the p53 consensus binding site having more than one monomer of RRRCWWGYYY (SEQ ID NO:3) upstream from and adjacent to said reporter gene; wherein said DNA construct is selected from the group consisting of a recombinant plasmid, a viral vector or an isolated molecule of DNA.

In another embodiment of the invention a method is provided of diagnosing tumor-inducing or hyperplastia-inducing strains of human papilloma virus (HPV) comprising: contacting cells or cell extracts of patients suspected of being infected by HPV with a p53-specific binding DNA fragment; and detecting the amount of wild-type p53 in said cells or cell extract which binds to said DNA fragment, absence of bound p53 indicating infection by strains of HPV which sequester p53.

These and other embodiments of the invention provide the art with new tools for detecting and remedying the loss of function of the most commonly mutated gene identified in human cancers. Further it provides methods for identifying agents which can suppress neoplastic growth.

BRIEF DESCRIPTION OF THE DRAWINGS

FIG. 1B. Tests for dependence on p53 and specific antibody. Cell lysates were produced by infection with vaccinia virus that did (+) or did not (−) contain an insert of wild-type p53 cDNA. Immunoprecipitation was performed with anti-p53 monoclonal antibodies (+) or normal mouse IgG (−).

FIG. 2A. Increasing quantities of wild-type and mutant $273^{his}$ p53, affinity-purified from a baculovirus expression system, were used to precipitate labelled $C_{BE}$ fragments. FIG. 2B. Lysates from a vaccinia virus system (Vac) producing the wild-type (wt), mutant ($175^{his}$), or no p53 protein (−), were used to immunoprecipitate labelled $C_{BE}$ fragments. Equivalent quantities of p53 were present in the wild-type and mutant p53 lysates, as assessed by Western blot. In the "Bac" lane, affinity-purified p53 produced in baculovirus-infected insect cells was used in place of the vaccinia-infected lysates.

FIGS. 3A and 3B. Fragment A and adjacent vector sequences in the 10d subclone of 772 $C_{BE}$. This differs from the published 772 $C_{BE}$ sequence (Genbank M25718) in the number of CTT repeats (bp 173–229) and in the presence of A instead of C at bp 116. FIG. 3B. Fragment B and adjacent vector sequences in the 8a subclone of Lambda 5R. A related sequence on file (Genbank X05913) varied somewhat from the Lambda 5R subclone studied.

FIG. 4A. Subfragments of fragment A (subclone 10d) were assayed by immunoprecipitation for their ability to bind wild-type p53 from vaccinia-infected cell lysates. Binding of at least 2% of the DNA added to the reaction was judged as a positive (+) result; lesser but significant binding was recorded as "+/−". Double Lines (=) denote fragment A sequences single lines (−) denote polylinker sequences of the vector, not originally present in fragment A (FIG. 1). Fragment 5mut1 had a G to T transversion at bp 120; 5mut2 had G to T transversions at bp 120 to 122. FIG. 4B. The fragment A (panels 1–4) and fragment B (panel 5) subfragments illustrated in FIG. 4A are labelled to the left of the bands. The "v" band in panel 4 corresponds to the 2.9 kb vector into which subfragment 6 was cloned. Subfragment 8 (panel 5) contained bp 104–238 of fragment B (see FIG. 3B). Control lanes (C) contained 2% of the labelled fragments used in the binding assays (B).

FIG. 5A. Methylation interference assay. "B"—bound DNA recovered from the immunoprecipitate. "C"—equivalent amount of control DNA fragments, not subject to binding reaction. Bound and control DNA samples were cleaved at methylated guanines and equal amounts separated by electrophoresis on a 6% denaturing gel. Dots represent methylation-sensitive sites (open for partial, solid for strong interference); some variation in band intensities occurred between assays, and only the reproducible changes are marked. FIG. 5B. Binding of "mutant" subfragments of fragment A (5mut1 and 5mut2) to purified baculovirus-produced p53 is compared to that of the normal subfragment 5 sequence. 5mut1 contains a T instead of G at bp 120, and 5mut2 contains Ts in place of Gs at bp 120, 121, and 122.

FIG. 8. Isolation of human genomic sequences which bound to p53.

FIG. 8B. Immunoprecipitation (IP) assays of cloned fragments. Clones of amplified and selected (AS) DNA were tested for the presence of p53-binding fragments by IP. For each clone, the bound DNA is shown in the B lane, adjacent to a control (c) lane containing 2% of the total end-labeled DNA used in the binding assay. In this representative experiment, eight binding fragments were identified, representing six unique genomic fragments. The inserts from the clones in lanes labeled 2, 3, 5, 9, 10, and 11 contained p53-binding fragments, while the other lanes contained none. The clones in lanes 2 and 5 each contained two binding fragments.

FIG. 9. Mapping of p53-binding sites by DNase I protection (DP) and methylation interference (MI). For each footprint, the first and fourth lanes contain control samples of the total labeled DNA, whereas the middle two lanes contain an equivalent amount of p53-bound DNA. DNA sequences corresponding to the p53-binding regions on strand 1 are shown in FIG. 10.

FIGS. 10A, 10B, 10C, and 10D. Definition of a consensus binding site for p53. The p53 binding site of 18 cloned human genomic DNA fragments, determined by footprinting methods are displayed along the central axis of symmetry which separates the two 10 bp consensus monomers. Nucleotides in capital letters represent identity of a genomic sequence to the consensus, whereas lower case letters identify disparity with the consensus. Sequences surrounding the consensus or separating the two 10 bp monomers are also shown in lower case. The ten synthetic oligonucleotides investigated for the ability to be bound by p53 are shown at the bottom. Oligonucleotides No. 6 to 10 were tested after cloning into plasmid vectors. Lower case letters represent vector-derived sequences. Combined nucleotide usage (%) within the two monomers of the consensus binding site is shown in the middle.

FIG. 11. Binding of synthetic oligonucleotides to wild-type (wt) and mutant p53 proteins.

FIG. 11A. The 10 b consensus monomer was insufficient for binding, whereas dimers in various orientations or multimers of the 10 bp consensus bound strongly to p53. For each sample, the control lane (C) contained 2% of the total DNA used in the binding reaction, and was composed of two fragments: 2.9 kb vector DNA fragment, and a fragment of 40 to 80 bp containing no insert (lane 9; XhoI plus PstI digest of pBluescript II SK+), the 10 bp consensus monomer sequence 5'-AGGCATGTCT-3' (SEQ ID NO:26) (lane 5), or multimers of this sequence arranged as indicated (lanes 1 to 4, 6, to 8). Bound DNA from the IP is shown in the B lanes.

FIG. 11B. Comparison of the ability of wild-type and mutant p53 to bind to the consensus dimer. In vitro translated p53 proteins were tested for the ability to bind the consensus dimer by IP. Two percent of the total DNA used for binding is shown in lane 1. Lane 7 shows binding to baculovirus-produced human wild-type p53 protein. Lanes 2 to 6 show binding of in vitro translated wild-type and mutant p53 proteins. The mutant p53 proteins contained changes at codon 143 (val to ala), 175 (arg to his), 248 (arg to trp), and 273 (arg to his).

FIG. 12. Reporter and expression constructs used in transfections are shown.

FIG. 13. Correlation of DNA-binding and transactivation is shown.

FIG. 14. Comparison of the ability of wild-type and mutant p53 to bind to a concatemerized binding sequence ($PG_{16}$), and lack of DNA-binding ability to $MG_{15}$ are shown. Each p53 form (as a rabbit reticulocyte preparation (Promega) made essentially as described in Kern, et al., Oncogene, 6:131–136 (1991); equalized for p53 quantity by immunoblot analysis, data not shown) was used to immunoprecipitate end-labeled DNA. C, control lanes, containing 2% of the labeled DNA used in the binding reaction. B, bound DNA recovered from the immunoprecipitate.

FIG. 15. Effects of varying the location of the binding sequence relative to the promoter are shown.

FIG. 16. Relative abilities of wild-type and mutant p53 to activate transcription are shown.

DETAILED DESCRIPTION OF THE INVENTION

Figures 1A, 1B:
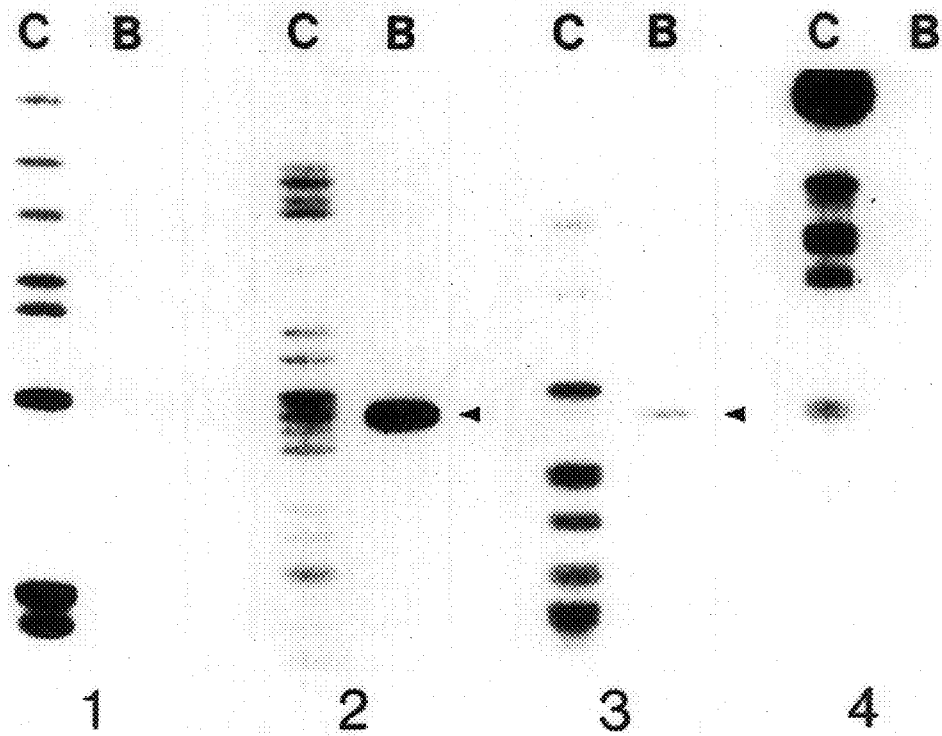
FIGS. 1A and 1B. Screening for fragments bound by p53 using an immunoprecipitation assay. Panel 1 contains the hFosAva2 clone; panel 2, 772 $C_{BE}$; panel 3, Lambda 5R; panel 4, a pool of clones with inserts of randomly cloned human genomic sequences. 772 $C_{BE}$ and Lambda 5R contain HinfI fragments (259 and 190 bp, respectively) which bound p53 relatively strongly (arrowheads). "C"—control lane, containing 2% of the labelled DNA used in the binding reactions. "B"—bound DNA recovered from the immunoprecipitate.

It is a finding of this invention that wild-type p53 protein binds specific fragments of human chromosomal DNA. Each of the fragments contains more than one monomer of the double-stranded motif 5'-RRRCWWGYYY-3' (SEQ ID NO:3) separated by 0 to 13 bp. Some of these sequences are found near origins of replication of certain animal viruses and animal cells. See Jelinek et al, Proc. Natl. Acad. Sci. USA, vol. 77, p. 1398–1402 (1980). Four mutant forms of p53 protein which are commonly found in human tumors do not have the ability to bind to these sequences. Thus, a function of p53 may be mediated by its ability to bind to specific DNA sequences in the human genome.

While-type p53 protein binds specifically to certain DNA sequences. Two previously isolated DNA fragments, called herein fragment A and fragment B, have been identified which contain residues which appear responsible for the binding. These residues are located within DNA segments which contain nucleotides 103–134 of SEQ ID NO:1 and nucleotides 104–198 of SEQ ID NO:2.

Fragment A contains sequences near a putative replication origin of the ribosomal gene cluster, while fragment B contains sequences that may allow adjacent sequences to replicate as extrachromosomal circles in HeLa cells (Sylvester, et al., Gene 84, 193, 1989). The TGCCT (SEQ ID NO:36) repeat present in the DNA binding region of both of these fragments has been observed in other potential replication origins. Thus p53 may be involved in the regulation of initiation of DNA synthesis by virtue of its binding.

It has been found that p53 will specifically bind to other sequences in the human genome with similar sequence motifs. Using a strategy coupling immunoprecipitation to "whole-genome PCR" (Kinzler, et al., Nucleic Acids Research, 17:3645–3653 (1989)), twenty human DNA fragments that bind to p53 have been identified. Each of the fragments contain a sequence which conforms to a dimer of the double-stranded motif 5'-RRRCWWGYYY-3' (SEQ ID NO:3) separated by 0 to 13 bp. These dimers directly mediate binding, as assessed by DNase I protection and methylation interference assays. The consensus dimers contain a striking symmetry, with four 5'-RRRCW-3' (SEQ ID NO:39) units oriented in alternating directions. A synthetic monomer containing the 10 bp consensus sequence is insufficient for binding, while the combination of two or more monomers bind strongly to wt p53, but negligibly to p53 mutants. Thus, more than one monomer appears to be required for binding. The spacing between monomers may be from 0 to 40 nucleotides, although all natural binding sites isolated have spacings of less than 15 nucleotides. The symmetry of the four half-sites within the consensus dimers suggests that p53 interacts with DNA as a tetrameric protein. The twenty unique clones shown in FIG. 10 allow the identification of adjacent genes which may be regulated by p53 and may mediate its growth-suppressive action.

A sequence which conforms to the consensus sequence need not have the exact sequence of the dimer. As shown in FIG. 10, p53-binding sequences can have nucleotides which are different than those designated. There can also be extra nucleotides inserted within the dimers. Nucleotides can also be missing from the dimer. Typically p53-binding sequences will vary from the consensus sequence at no more than 5 nucleotide positions.

It is an additional finding of the present invention that wild-type p53 can activate the expression of genes adjacent to a specific binding site. Moreover, the level of in vivo transactivation is proportional to the in vitro strength of DNA-binding. Mutant p53 encoded by oncogenic p53 genes (i.e., those found in cancer cells of human patients), completely lose the ability to transactivate. In addition the mutant p53 proteins exert a dominant-negative effect, dramatically reducing the transactivating activity of wild-type p53.

Based on the sequence information of the p53 specific-DNA-binding fragments, a number of diagnostic and therapeutic methods have been devised. According to one such method, cell lysates are tested for the presence or absence of wild-type p53 by virtue of its specific DNA binding ability. As it is known for various cancers and stages of cancers that one or both of the p53 alleles in tumor tissues can be mutant, testing for the presence or absence of wild-type p53 protein can provide diagnostic and prognostic information regarding a tumor and the patient. The cells to be tested are typically isolated from a tissue suspected of being neoplastic. Preferably the tissues are carefully prepared and isolated so that non-neoplastic tissues are not mixed with the neoplastic tissues, which can confound the analysis. Means for separating neoplastic tissues from non-neoplastic tissues are known in the art and include dissection of paraffin or cryostat sections, as well as use of flow cytometry. A cell lysate can be prepared from the tumor tissue according to any method known in the art. The cell lysate is then incubated with DNA fragments which are known to bind the wild-type p53 protein, under conditions which are conducive to such DNA/protein interactions. Alternatively, a histological sample can be analyzed by incubation with DNA fragments, as described for cell lysates.

It is known that p53 also binds non-specifically to DNA. Specific binding can be distinguished from non-specific binding by any means known in the art. For example, specific binding interactions are stronger than non-specific binding interactions. Thus the incubation mixture can be subjected to any agent or condition which destabilizes protein/DNA interactions such that the specific binding reaction is the predominant one detected. Alternatively, as taught more specifically below, a non-specific competitor, such as dI-dC, can be added to the incubation mixture. If the DNA containing the specific binding sites is labelled and the competitor is unlabeled, then the specific binding reactions will be the ones predominantly detected upon measuring labelled DNA.

According to one embodiment of the invention the DNA which is bound to p53 is separated from unbound DNA by immunoprecipitation with antibodies which are specific for p53. Use of two different monoclonal anti-p53 antibodies may result in more complete immunoprecipitation than either one alone. Unbound DNA remains in suspension. The amount of DNA which is in the immunoprecipitate can be quantitated by any means known in the art. According to one aspect of the invention, the DNA fragment is labelled with a detectable moiety, such as a radioactive moiety, a colorimetric moiety or a fluorescent moiety. Techniques for so labelling DNA are well known in the art. According to other embodiments of the invention, p53 which binds to the specific DNA sequence of the present invention can be detected by gel shift assays (Tan, Cell, 62:367, 1990), nuclease protection assays (see Example 9, infra), or methylase interference assays (see Example 9, infra).

According to another embodiment of the invention, after incubation of p53 with specific binding DNA fragments all components of the cell lysate which do not bind to the DNA fragments are removed. This can be accomplished, among other ways, by employing DNA fragments which are attached to an insoluble polymeric support such as agarose, cellulose and the like. After binding, all non-binding components can be washed away, leaving p53 bound to the DNA/solid support. The p53 can be quantitated by any means known in the art. It can be determined using an immunological assay, such as an ELISA, RIA or Western blotting.

The diagnostic assay of the present invention has applicability not only with regard to cancers which are known to involve mutation of p53, but also with regard to human viruses such as human papilloma virus (HPV). HPV protein E6 binds tightly to wild-type but not mutant p53. See Werness et al., Science, 248, 76–69 (1990). This tight binding is likely to block the interaction of p53 with its specific DNA binding sequences. By testing cells or cell extracts suspected of being infected with potentially tumor-inducing or hyperplastia-inducing strains of HPV or possible other viruses, infected cells can be identified, because the E6 protein of the infected cells will have sequestered the wild-type p53, rendering it unable to bind to its specific DNA binding sequences. Such assays may be performed on cell extracts or on histological specimens.

According to the present invention a method is also provided of supplying wild-type p53 function to a cell which carries mutant p53 alleles. The wild-type p53 gene or a part of the gene may be introduced into the cell in a vector such that the gene remains extrachromosomal. In such a situation the gene will be expressed by the cell from the extrachromosomal location. If the mutant p53 genes present in the cell are expressed, then the wild-type p53 gene or gene portion should be expressed to a higher level than that of the mutant gene. This is because the mutant forms of the protein are thought to oligomerize with wild-type forms of the protein. (Eliyahu et al., Oncogene, vol. 3, p. 313, 1988.) If a gene portion is introduced and expressed in a cell carrying a mutant p53 allele, the gene portion should encode a part of the p53 protein which is required for non-neoplastic growth of the cell. More preferred is the situation where the wild-type p53 gene or a part of it is introduced into the mutant cell in such a way that it recombines with the endogenous mutant p53 gene present in the cell. Such recombination would require a double recombination event which would result in the correction of the p53 gene mutation. Vectors for introduction of genes both for recombination and for extrachromosomal maintenance are known in the art and any suitable vector may be used.

Polypeptides or other molecules which have p53 activity may be supplied to cells which carry mutant p53 alleles. The active molecules can be introduced into the cells by microinjection or by liposomes, for example. Alternatively, some such active molecules may be taken up by the cells, actively or by diffusion. Supply of such active molecules will effect a less aggressive state of neoplasia.

According to the present invention compounds which have p53 activity are those which specifically complex with a p53-specific DNA binding site. Wild-type p53 is one such compound, but portions of p53 which retain the ability to bind to p53-specific binding sites may also be used. Oligonucleotides and oligonucleotide containing nucleotide analogs are also contemplated among those compounds which are able to complex with a p53-specific DNA binding site. Although applicants do not wish to be bound by any particular theory, it is believed that oligonucleotides bind double-stranded DNA to form triplexes. Such triplexes have been shown to block transcription of certain genes, as well as protect the DNA binding sites from the action of enzymes such as DNA methylases. Although originally such oligonucleotides were thought to require only or predominantly pyrimidenes (cytosine and thymine), purines have also successfully been incorporated into triplex forming oligonucleotides. Particular oligonucleotides which may be used include: nucleotides 140–162 of SEQ ID NO:2, nucleotides 128–158 of SEQ ID NO:1, nucleotides 114–123 of SEQ ID NO: 1, or portions thereof having at least ten nucleotides.

Oligonucleotides containing nucleotide analogs or otherwise modified oligonucleotides may also be useful in the formation of complexes with double-stranded DNA. For example, certain modifications to the 3'-terminus can be employed to reduce the susceptibility of the oligonucleotide to nuclease degradation. Moieties which may be appended to the 3'- or 5'-termini include a substituted or unsubstituted amino group, polyethylene glycol, polylysine, acridine, dodecanol, and cholesterol. Oligonucleotides and oligonucleotides containing nucleotide analogs which may be used include methylphosphonates, aminomethylphosphonates, phosphorothioates, phosphorodithioates, substituted or unsubstituted phosphoramidates, oligoribonucleotides, oligodeoxyribonucleotides, alpha-oligonucleotides and mixtures thereof. Other modifications to oligonucleotides may be desirable to increase the uptake by cells or nuclei of the oligonucleotides or to decrease nuclease sensitivity. All such modifications are within the contemplation of the invention.

Switchback linkers may also be incorporated into the midst of an oligonucleotide or analog. Such linkers are taught by Riordan and Martin (Nature, 350, 452, 1991). They are designed by molecular modeling to provide the proper spacing between portions of an oligonucleotide which are to interact with different strands of a double-stranded DNA molecule. Examples of oligonucleotides having such linkers include the following: TTGCCTTGCCT-switchback linker-CCT-switchback linker-CTTGCCT (corresponding to nucleotides 105–125 of the double-stranded sequence represented by SEQ ID NO:1) or portions thereof.

Single-stranded, linear or circular oligonucleotides containing nucleotide analogs which are able to complex specifically with all or part of a p53-specific binding site as described above are also contemplated as part of the invention. (See Kool, J. Am. Chem. Soc., vol. 113:625–626, 1991, with regard to circular oligonucleotides.) Such oligonucleotides containing nucleotide analogs should comprise at least about ten nucleotides in length in order to have the requisite specificity with respect to the entire human genome. Oligonucleotides or oligonucleotides containing nucleotide analogs which are able to complex specifically with part of a p53 binding site as well as with adjacent sequences are also contemplated as part of the invention. The oligonucleotides or oligonucleotides containing nucleotide analogs will preferably bind to the identified p53 binding regions. However, other binding regions in the human genome may well be found which are also suitable targets for the oligonucleotides or analogs of the present invention. These other binding sites may well be the primary targets of p53; complexation of these sites may inhibit the unregulated growth which characterizes neoplastic cells.

Double-stranded DNA fragments which comprise a p53-specific DNA binding site and are attached to an insoluble polymeric support are also contemplated by this invention. The support may be agarose, cellulose, polycarbonate, polystyrene and the like. Such supported fragments may be used in screens to identify compounds which bind to p53-specific DNA binding sites. Similarly, such supported fragments may be used to perform diagnostic tests on cell lysates from suspected tumor tissues. They may also be used in assays used to screen potential chemotherapeutic agents, as discussed infra.

Although any method can be employed which utilizes the p53-specific DNA binding sites of the present invention, two particular methods are disclosed for screening for additional compounds that bind to p53-specific DNA binding sites. According to one method a test compound is incubated with a supported DNA fragment, as described above. The amount of test compound which binds to the supported DNA fragment is determined. This determination can be performed according to any means which is convenient. For example, the amount of a compound which can be removed after incubation with the supported fragment can be compared to the amount originally applied. Alternatively, the test compound can be labelled and the amount which binds to the supported fragment can be assayed directly. In order to render this screening method more specific, soluble DNA fragments which do not contain the p53 DNA binding sequence can be added to the incubation mixture. The soluble fragments would not have the ability to specifically bind to p53 wild-type protein.

According to another screening method for compounds to simulate the specific DNA binding activity of p53, test compounds are incubated with supported DNA fragments as described above. However, in this method wild-type p53 protein is also added to the incubation mixture. The amount of p53 protein which binds to the DNA fragment is measured using methods as described above. The amount of p53 protein bound is compared to the amount which binds in the absence of the test compound. Any diminution of p53 binding which results from the presence of the test compound is presumptively due to the competition of the test compound with p53 for the specific DNA binding sites of the supported fragments. Direct binding of the test compound to the binding site fragments can be confirmed using the assay described above.

The presence or absence of p53 genes or gene products can also be detected in body samples, such as, serum, stool, or other body fluids, such as urine and sputum. The same techniques discussed above for detection of the presence or absence of gene products in tissues can be applied to other body samples. By screening such body samples, a simple early diagnosis can be achieved for many types of cancers. In addition, the progress of chemotherapy or radiotherapy can be monitored more easily by testing such body samples for the presence or absence p53 genes or gene products.

The methods of the present invention for diagnosis and therapy of neoplastic tissue is applicable across a broad range of tumors. These include lung, breast, brain, colorectal, bladder, mesenchyme, prostate, liver as well as stomach tumors. In addition the method may be used in leukemias and osteosarcomas. It thus appears that the p53 gene has a role in the development of a broad range of tumors. The methods of diagnosis and therapy of the present invention are applicable to any tumor in which p53 has a role in tumorigenesis. The diagnostic method of the present invention is useful for clinicians so that they can decide upon an appropriate course of treatment. For example, a tumor displaying loss of both p53 alleles suggests a more aggressive therapeutic regimen than a tumor displaying loss of only one p53 allele.

Compounds which have p53-specific DNA-binding activity, including wild-type p53 protein, polypeptides corresponding to portions of wild-type p53 protein, oligonucleotides and oligonucleotide containing nucleotide analogues, as well as other organic molecules can also be administered to humans and animals as a pharmaceutical and therapeutic composition. Effective amounts will be administered to cause neoplastic cells to become less aggressively neoplastic or even to stop the growth of the neoplastic cells entirely. Generally, such amounts will be in the range of 10 ng to 10 μg per dose per person or other animal. The therapeutic compounds can be prepared in any conventional pharmaceutical excipient, such as physiological saline or other physiologically compatible aqueous buffer. Typically, the compounds will be administered by injection, either intravenous or intramuscular. However, other administration methods as are known in the art and may be used to administer the compounds of the present invention.

As a result of the discoveries of the present invention, screening methods can be devised to isolate chemical agents which may have use in cancer therapy. Specifically, agents can be screened for the ability to affect the structure of mutant p53 molecules so that their ability to bind and/or transactivate at specific-DNA-binding sites is restored. The necessary components for such a screening method are provided by this invention and include DNA molecules which contain more than one monomer of the sequence RRRCWWGYYY (SEQ ID NO:3), and mutant p53 proteins which are found in tumors.[1]/

[1]/Not all mutations in p53 destroy specific-DNA-binding ability. For example, mutations in phosphorylation sites of p53 have been made and tested; they retain binding activity. Such mutations have never been found in tumors. Mutations in p53 which are found in tumors are termed oncogenic herein.

One such prescreening method is a binding assay in which the amount of binding of a p53 mutant protein to a DNA molecule which comprises the consensus binding site (or a conforming sequence) is measured. The amount of binding is also measured for a p53 mutant protein in the presence of a test substance. If the test substance increases the amount of p53 binding, then the test substance is a candidate for use in anti-tumor therapy. Further testing will be desirable before use in humans is attempted.

Methods for measuring the amount of binding can be any which are known in the art. See, e.g., Tan, et al., Cell, 62:367–377 (1990). One particular method employs immunoprecipitation. Briefly, purified p53 or a lysate of a cell expressing p53 is incubated with radiolabeled DNA and anti-p53 antibodies under conditions where proteins bind to DNA. Protein A-Sepharose and poly-dIdC-poly-dIdC are then added for an additional incubation. A pellet is formed and washed and the proteins are removed by digestion with a protease, and DNA is obtained by phenol extraction. The extracted DNA is then analyzed by electrophoresis and quantified. Quantitation of the DNA can be by autoradiography, for example. The amount of DNA immunoprecipitated is proportional to the amount of binding of the p53 protein to the DNA.

According to another method, the ability of a mutant p53 protein from a tumor to transactivate transcription in vitro is assessed with and without a test substance. If the test substance increases the amount of transcription activated by the p53, then the test substance is a candidate for use in anti-tumor therapy. Transcriptional activation is measured using a transcription construct which comprises a reporter gene encoding a convenient assayable enzyme activity, such as chloramphenicol acetyltransferase or β-galactosidase, and an upstream p53 consensus binding site (or a conforming sequence). The binding site must be upstream, although the distance from the start of transcription is not critical. The binding site, which is adjacent to the reporter gene, may be from 0 to 1 kb upstream. In vitro transcription assay systems are well known in the art. See, e.g., Lue, *Science*, 246, 661–664 (1989).

Figure 12A:
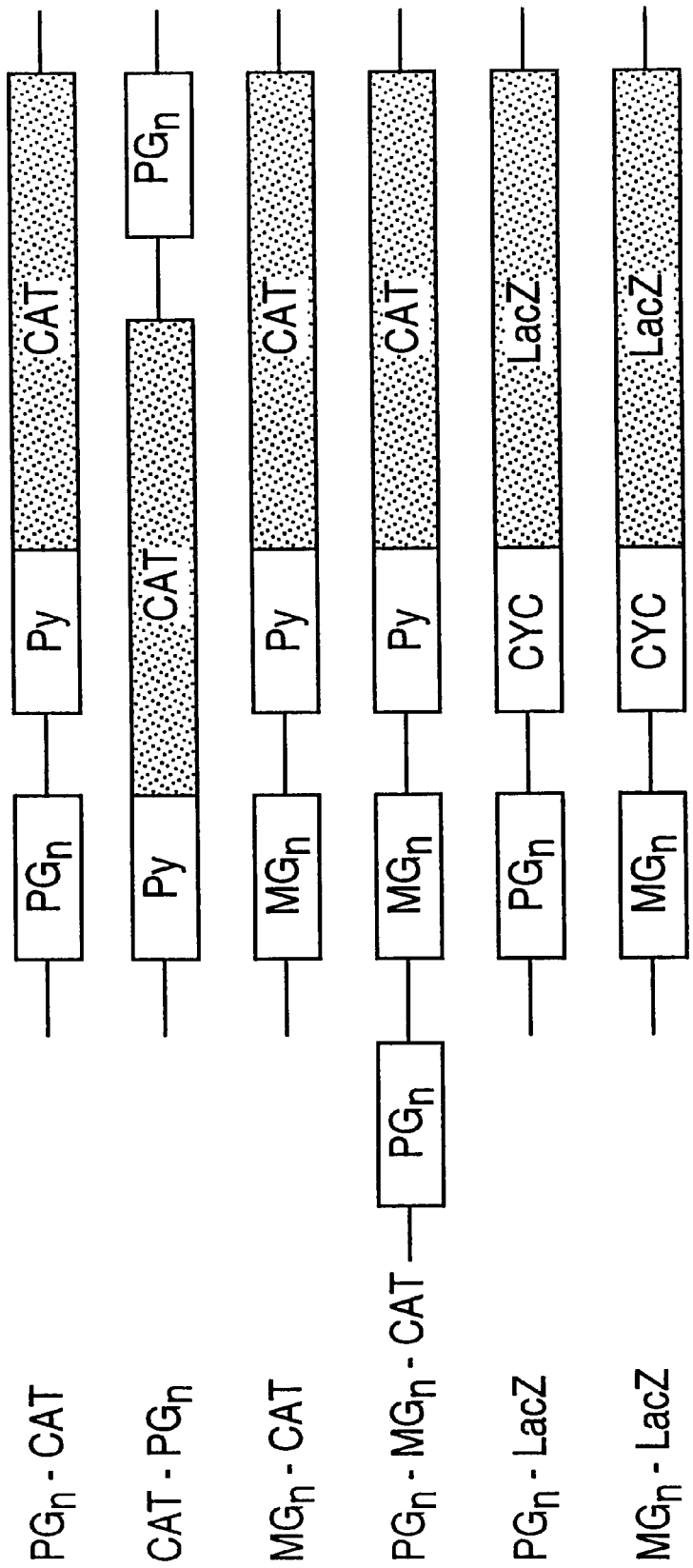
FIG. 12A. Reporter constructs in pBluescript II SK+ vector (Stratagene). $PG_n$, concatemers of n copies of the p53 binding sequence PG. $MG_n$, concatemers of the mutated sequence, which does not bind p53. CAT, the chloramphenicol acetyltransferase coding sequence. LacZ, the β-galactosidase coding sequence. Py, the early gene promoter from polyomavirus. CYC, the yeast cytochrome c gene promoter.

According to still another method, transcriptional activation can be measured in a cell containing a mutant p53 protein which has been transfected with a reporter gene construct comprising a gene encoding an assayable product, such as an enzyme or antigen, with a p53 consensus binding site (or conforming sequence) adjacent and upstream therefrom. The transfected cells are treated with a test substance. If the amount of transactivation caused by the mutant p53 is enhanced by the test substance, then the substance is a candidate for anti-tumor therapy presumably due to its interaction with the mutant protein. A particular transactivation assay (transient expression assay) is described in Example 12, infra. Particular reporter constructs are shown in FIG. 12A. Others may be used within the scope of the invention. Alternatively, if the transfected cell contains wild-type p53 diminished activation would indicate that the test substance competes with p53 for binding sites.

In another embodiment of the invention, oligonucleotides can be isolated which restore to mutant p53 proteins the ability to bind to the consensus binding sequence or conforming sequences. Mutant p53 protein and random oligonucleotides are added to a solid support on which p53-specific-binding DNA fragments are immobilized. Oligonucleotides which bind to the solid support are recovered and analyzed. Those whose binding to the solid support is dependent on the presence of the mutant p53 protein are presumptively binding the support by binding to and restoring the conformation of the mutant protein.

Transient expression constructs are conveniently made on plasmids and viral vectors, so that they can be propagated. These can also be used in vitro for transcription assays in the presence of RNA polymerase, ribonucleotides, and other cofactors.

EXAMPLES

Example 1

This example demonstrates the screening methods used to identify a p53 sequence-specific binding site.

In an attempt to identify a possible sequence-specific binding site, numerous cloned DNA sequences were screened using an immunoprecipitation technique. The immunoprecipitation assay for DNA-binding was modified from R. D. G. McKay, J. Mol. Biol. 145. 471 (1981). Binding reactions included 5 µl of vaccinia-infected cell lysate or purified baculovirus p53 preparations, 95 µl binding buffer (20 mM Tris pH 7.2, 100 mM NaCl, 10% glycerol, 1% NP-40, 5 mM EDTA), 6–20×10$^4$ dpm $^{32}$P-labelled DNA, 4 µl (0.4 µg) pAb421 and 4 µl (0.4 µg) pAb1801 anti-p53 purified monoclonal antibodies (Oncogene Science), at 4° C. for 30 min. 1.5 mg protein A-Sepharose (Sigma) and 12.5 µg poly-dIdC-poly-dIdC (Pharmacia), in 25 µl binding buffer, were added and the reactions rotated end-over-end at 4° C. for 30 min. The pellet was washed twice with binding buffer and the proteins digested with SDS-proteinase K, then extracted with phenol and chloroform. The DNA was ethanol-precipitated and dissolved in electrophoresis sample buffer. The fragments were separated on a Tris-borate nondenaturing polyacrylamide (7, 10, or 12%) gel. The gel was fixed and dried for autoradiography.

Recombinant vaccinia viruses expressing p53 from the 40K promoter were isolated and purified as described in J. Lyons et al., Infec. and Immun. 58, 4089 (1990).

Vaccinia-infected cell lysates were prepared as follows: the indicated cells (about 2.5×10$^7$) were infected (MOI 2), harvested at 24 hrs and lysed in 2 ml lysis buffer (PBS containing 5 mM EDTA, 0.5% NP-40, 0.5 mM PMSF, 10 µg/ml TPCK, 1 µg/ml aprotinin, 10 µg/ml trypsin inhibitor, 1 µg/ml leupeptin). Cell debris was pelleted at 16,000×g and the supernatant UV-irradiated (0.5 Joules). The supernatant was frozen in aliquots at −80° C. and found to be stable for at least 6 months.

Baculovirus-produced p53 was purified as described in P. N. Friedman, et al., Proc. Natl. Acad. Sci. USA, 87, 9275 (1990); while the presence of an accessory cofactor in the purified preparation cannot be excluded, SDS-polyacrylamide gel electrophoresis of the preparation revealed only a single polypeptide migrating at 53 kD upon silver-staining.

Two classes of clones were tested. The first class consisted of 400 clones containing inserts of 300 to 1000 base-pairs obtained randomly from the human genome. The second class consisted of cosmid and plasmid clones chosen because they contained sequences which might be important in normal growth control. Random human genomic clones were prepared from a partial MboI digest of human DNA; 300–1000 bp fragments were purified and ligated to EcoRI linkers, then cloned into the EcoRI site of pBluescript II (Stratagene). Clones selected because they might be important in normal growth included SP65hFosAva2, containing regulatory sequences from the fos gene, obtained from T Curran; 772 C$_{BE}$ (J. E. Sylvester, R. Petersen, R. D. Schmeckel, Gene, 84, 193 (1989)), from J. Sylvester; a 4.4 kb BglII subclone of Lambda 5R (R. Misra, et al., Nucl. Acids Res. 17:8327 (1989)), from C. Schmid; the c-myc clone was HSR-1 (K. Alitano, et al., Proc. Natl. Acad. Sci. USA, 80, 1707 (1983)) from J. Bishop. Cosmids containing the entire p53 genomic region were from Y. Nakamura; cosmids including the entire DHFR amplicon from hamster cells (B. Anachkova and J. L. Hamlin, Mol. Cell Biol. 9, 532 (1989)) were from J. Hamlin.

Each clone was digested with an appropriate restriction endonuclease, end-labelled with $^{32}$P, and incubated with p53 protein from a lysate of cells infected with a recombinant vaccinia virus expressing p53 protein. Labelled DNA fragments which bound to p53 were then recovered by immunoprecipitation with monoclonal antibodies against p53. Of the more than 1400 restriction fragments tested, only two bound reproducibly to p53 under the experimental conditions used: a 259 basepair HinfI fragment (fragment A) of clone 772 $C_{BE}$ (Panel 2, FIG. 1A), and a 190 basepair HinfI fragment (fragment B) of clone Lambda 5R (Panel 3, FIG. 1A); these fragments bound to a far greater extent than any of the other labelled fragments of larger or smaller size present in the same assay mixes.

Example 2

This example demonstrates that the immunoprecipitation of fragment A is dependent on both p53 protein and anti-p53 antibodies.

The immunoprecipitation assay was performed on fragment A as described in Example 1. Cell lysates were produced by infection with vaccinia virus that did or did not contain an insert of wild-type p53 DNA. Either anti-p53 antibodies were used or normal mouse IgG was used.

Lysates from cells infected with wild-type vaccinia virus (devoid of p53) were not able to specifically immunoprecipitate fragment A (FIG. 1B). Similarly, the detection of the precipitation of fragment A was dependent on the presence of anti-p53 antibodies (FIG. 1B). The binding was evident in lysates prepared from either human HeLa cells or monkey BSC40 cells infected with vaccinia virus and expressing wild-type p53 (FIG. 1B).

Figure 2A:
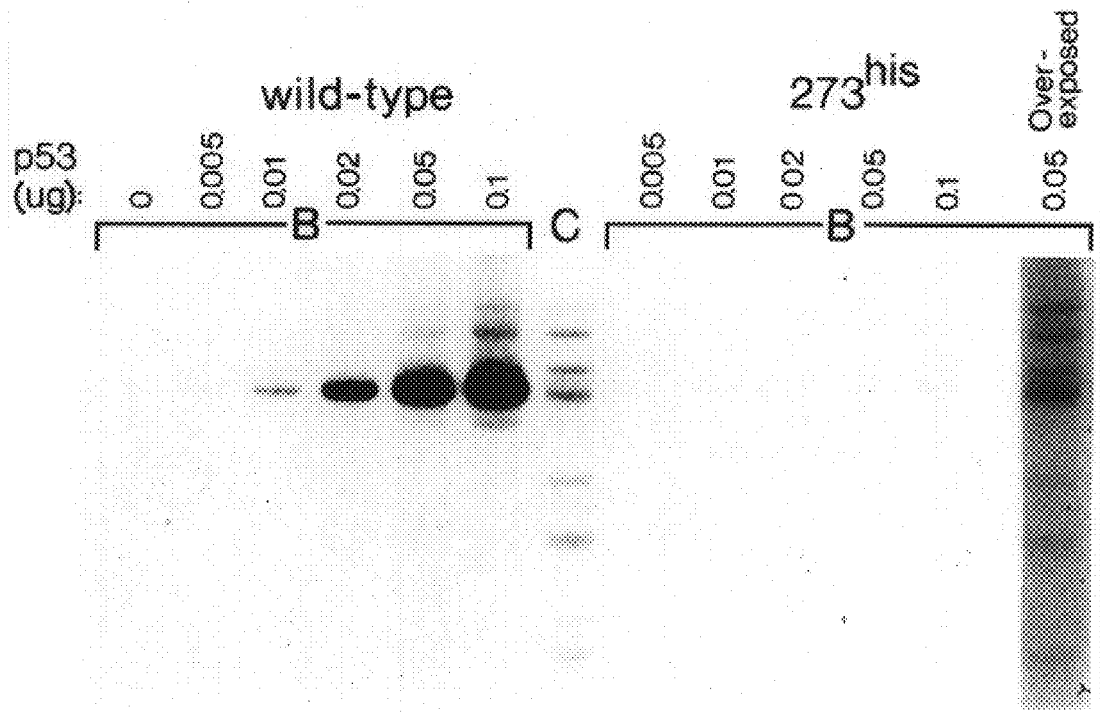
FIGS. 2A and 2B. Relative abilities of wild-type and mutant p53 to precipitate fragment A. "C"—control lanes, containing 2% of the labelled DNA used in the binding reaction, "B"—bound DNA recovered from the immunoprecipitate.
Figure 2B:

Affinity-purified baculovirus-produced wild-type p53 protein was substituted for the vaccinia-infected cell lysates in the immunoprecipitation assay and found to bind fragment A strongly (FIG. 2A). This suggested that the binding to fragment A was an intrinsic property of the p53 polypeptide and not dependent on other factors present in the vaccinia virus-infected cell lysates.

Example 3

This example demonstrates that p53 mutant proteins found in human tumors fail to bind to fragment A.

Increasing quantities of wild-type and mutant $273^{his}$ p53 protein, affinity purified from a baculovirus expression system, were used to immunoprecipitate labelled fragments from $C_{BE}$. See FIG. 2A. The proportion of fragment A bound to wild-type p53 protein increased in tandem with the amount of p53 added to the assay mixture. (FIG. 2A) In contrast, fragment A did not specifically bind to a mutant form of p53 ($273^{his}$) protein even at the highest p53 protein concentration used. The $273^{his}$ mutation is the most common p53 mutant identified in human tumors. Another p53 mutant ($175^{his}$) protein commonly found in human tumors also failed to bind to fragment A (FIG. 1B).

Example 4

This example defines the particular sequences within fragment A that allow it to bind to wild-type p53 protein.

Fragment A was subcloned, and the 259 bp insert from the subclone (10d, SEQ ID: 1 and FIG. 3A) bound to p53 as expected. A strategy based on the polymerase chain reaction (PCR) and restriction endonuclease digestion was used to generate subfragments of this clone.

Figure 4A:
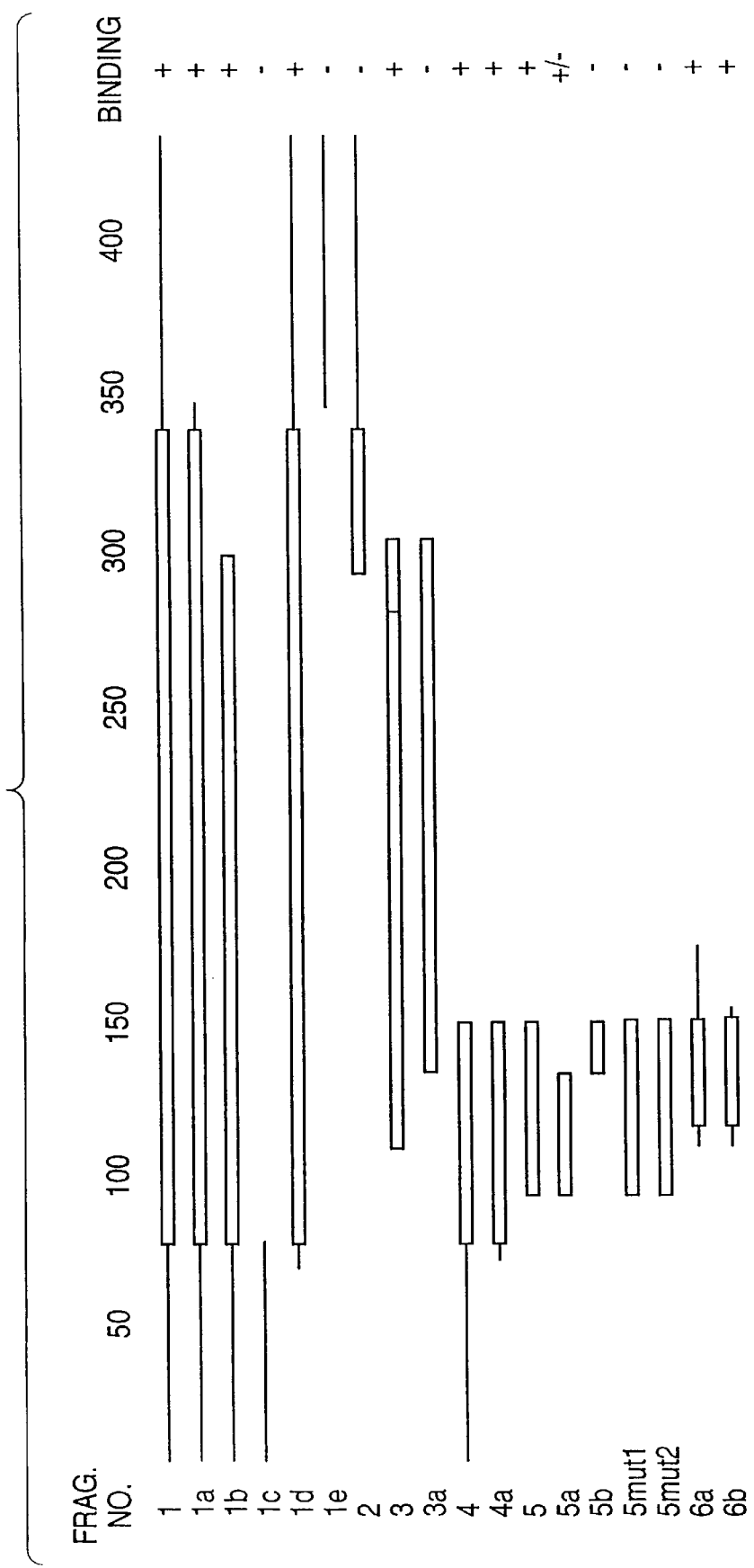
FIGS. 4A and 4B. Binding of various subfragments of fragments A and B to p53 from vaccinia-infected cell lysates.
Figure 4B:
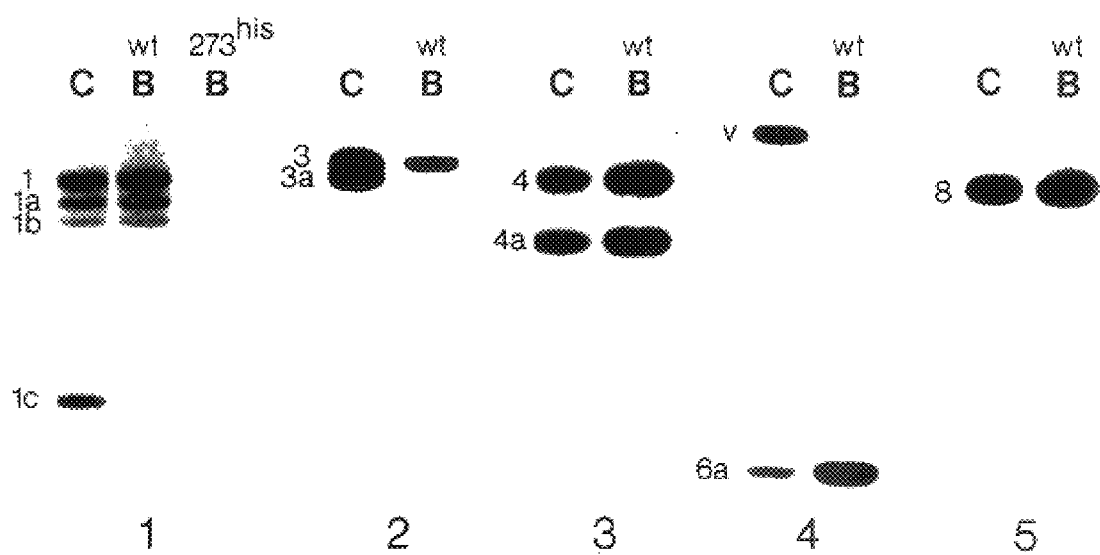

One primer for each PCR was labelled with $^{32}P$ at the 5' end with T4 polynucleotide kinase in a 5 µl reaction, and the kinase inactivated at 70° C. for 5 min. PCR contained 350 ng of each of the appropriate primers and approximately 50 ng plasmid template in a 50 µl reaction, using 25 cycles and the PCR conditions specified in Baker S J, et al., Cancer. Res., 50:7717 (1990). The products were extracted with phenol and chloroform, ethanol-precipitated, and dissolved in 3 mM Tris, 0.2 mM EDTA prior to binding. Subfragment 1 contained bp 1 to 425 of subclone 10d of fragment A (FIG. 3A); subfragments 1a, 1b, 1c, 1d, and 1e were generated by digestion of subfragment 1 with BamHI, MboI, HindIII, HindIII, and BamHI, respectively, from fragment 1. Subfragment 2, contained bp 283 to 425. Subfragment 3a was generated by digestion of subfragment 3 (bp 106 to 294) with Hae III. Subfragment 4a was produced from subfragment 4 (gp 1 to 141) by Hind III digestion. Subfragments 5a and 5b were products of the HaeIII digestion of subfragment 5 (bp 87 to 141). "Mutant" subfragments 5mut1 and 5 mut2 were produced using primers P3m1 (5'-GAAAGAAAAGGCAAGGCCAGGAAAGT-3') (SEQ ID NO:34) and P3mut2 (5'-GAAAGAAAAGGCAAGGCCATTAAAGT-3') (SEQ ID NO:35) and were identical to subfragment 5 except for the positions underlined in the primers. Subfragment 6 contained bp 106 to 138, and the insert was excised by restriction with HindIII and BamHI to generate 6a or with HindIII and EcoRI to generate 6b. Subfragment 3, including basepairs 106 to 294 (FIG. 4B, panel 2), bound well to p53 as did subfragment 4, containing basepairs 1 to 141 (FIG. 4B, panel 3). This and similar assays done with additional subfragments (FIGS. 4A and 4B) localized the critical sequences to basepairs 106 to 141. This segment contained three repeats of the sequence TGCCT (SEQ ID NO:36) (FIG. 3A). Digestion of subfragment 3 with HaeIII (cleaving between bp 125–126 and removing two of the TGCCT (SEQ ID NO:36) repeats) greatly reduced this binding (FIG. 4B, subfragment 3A, panel 2), suggesting that a critical sequence lay at or near this restriction site and that a single TGCCT (SEQ ID NO:36) repeat was not sufficient for binding. Additional subfragments were tested (#5, bp 87 to 141, FIGS. 4A and 5B; #6, bp 106 to 138, FIGS. 4A and 4B, panel 4), and it was established that a 33 bp insert containing three TGCCT (SEQ ID NO:36) repeats providing binding capability.

Example 5

This example demonstrates that certain G residues are critical for binding of p53 to fragment A.

Figure 5A:
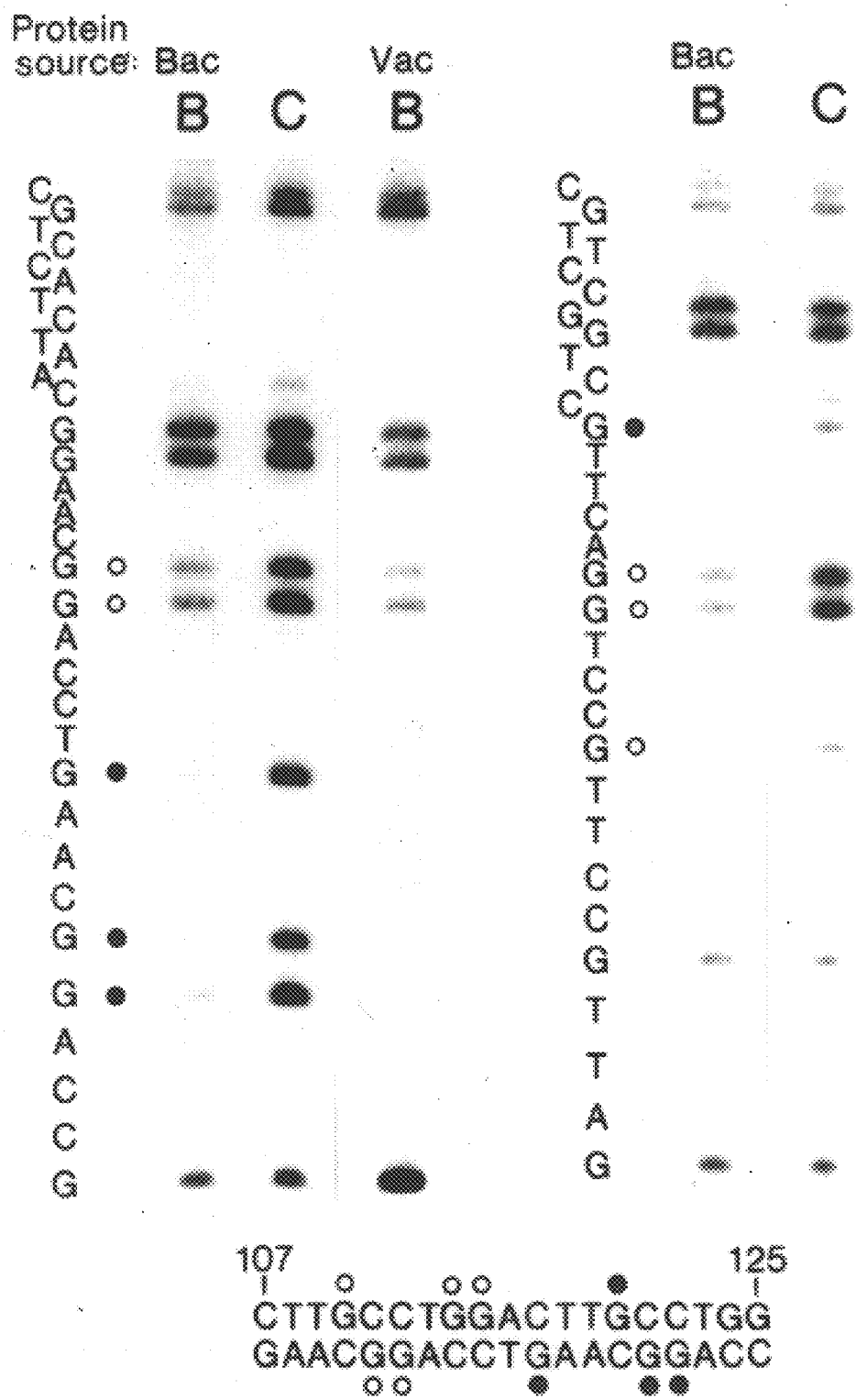
FIGS. 5A and 5B. Effects of methylation and point mutations in fragment A on DNA-binding.

We studied the requirements for binding at the single nucleotide level using a methylation interference assay. PCR products labelled at one end were generated using primers labelled with T4 polynucleotide kinase (US Biochemicals). The product of each PCR reaction was purified by polyacrylamide gel electrophoresis, eluted from a crushed gel slice in 500 mM ammonium acetate, extracted with phenol and chloroform, and precipitated with ethanol. $2 \times 10^6$ dpm of DNA was methylated at guanine residues using dimethylsulfate as described (T. Maniatis, E. F. Fritsch, J. Sambrook, *Molecular Cloning: A laboratory Manual,* 1st ed., Cold Spring Harbor Laboratory, 1983, p. 477), ethanol-precipitated and dissolved in 10 µl 3 mM Tris, 0.2 mM EDTA. 0.5 µl was removed as the DNA control. 4.5 µl was added to a binding reaction containing baculovirus-produced p53 or vaccinia-infected cell lysates. The precipitated DNA was purified by SDS/proteinase K digestion, extracted with phenol-chloroform, and ethanol-precipitated. The control DNA and precipitates of bound DNA were cleaved with piperidine at the methylated sites. Equivalent amounts of labelled DNA were loaded and separated on a denaturing polyacrylamide (14.5%) sequencing gel, which was fixed and dried for autoradiography. Subfragment 5, demonstrating efficient binding (FIGS. 4A and 5B) was methylated in vitro, and immunoprecipitated after binding to p53. The bound DNA was then cleaved with piperidine at methylated residues and separated by electrophoresis on a sequencing gel. Assay of one strand (FIG. 5A, right) demonstrated that methylation at the G at bp 120 significantly interfered with binding. On the opposite strand (FIG. 5A, left), the most effective interference was produced by methylation at G residues at bp 117, 121, and 122. Partial interference was also produced by methylation at nearby G sites (bp 110–112, 114, and 115). Thus, the methylation interference assay pinpointed one of the central TGCCT (SEQ ID NO:36) repeats (centered at basepair 121) and adjacent basepairs as critical for binding.

Figure 5B:
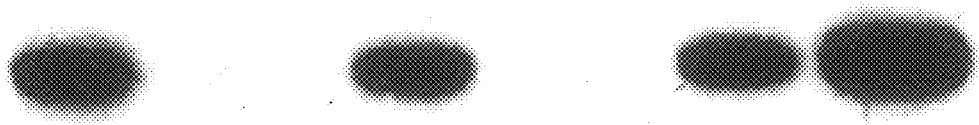

To obtain independent evidence of the specificity for the G residues identified by methylation interference, in vitro mutagenesis was used. A DNA fragment was generated that was identical to subfragment 5 except for the substitution of G at bp 120, 121, and 122 with T residues. This "mutant" subfragment (#5mut2) bound poorly to p53 (FIG. 5B). A fragment identical to subfragment 5 except for a single basepair (T substituted for G at bp 120 ) was then tested. This fragment (#5mut1) also did not bind appreciably (FIG. 5B).

Example 6

This example defines the region of fragment B which is important for p53 binding.

Fragment B was subcloned (sequence in FIG. 3B and SEQ ID NO:2). Interestingly, this fragment had two repeats of the TGCCT (SEQ ID NO:36) motif (centered at bp 135 and 152). A PCR strategy similar to that used for fragment A was used to demonstrate that a 95 basepair subfragment (bp 104 to 198), which contained both of these repeats, was sufficient for binding (FIG. 4B, panel 5).

Example 7

This example shows that expression of the wild-type p53 gene in human colorectal carcinoma cells dramatically inhibits their growth and that a mutant p53 gene cloned from a human colorectal carcinoma was incapable of exerting such inhibition.

The colorectal carcinoma lines SW480 and SW837, which are representative of 75% of colon carcinomas, have each lost one copy of chromosome 17p (including the p53 gene) and the remaining p53 allele is mutated (Baker, et al., Science 244, 217 (1989); Nigro et al, Nature 342, 705 (1989)). The SW837 line contains an arginine to tryptophan mutation at codon 248 (Nigro, supra). The SW480 line contains two point mutations, arginine to histidine at codon 273 and proline to serine at codon 309 (Nigro, supra.). The substitutions at codon 248 and 273 are typical of those observed in human tumors, occurring within two of the four mutation "hot spots" (Nigro, supra).

For the transfection studies, we constructed a vector, pCMV-Neo-Bam, engineered to contain two independent transcription units. The expression vector pCMV-Neo-Bam was derived from plasmid BCMGNeo-mIL2 (Karasuyama, et al., J. Exp. Med. 169, 13 (1989) by excision of the human beta globin sequences and bovine papilloma virus sequences with Bam HI and Not I. Next, the interleukin 2 (IL-2) sequences present at the unique Xho I site were removed, and the Xho I site was changed to a Bam HI site by linker addition. The vector included CMV promoter/enhancer sequences, which could drive expression of the insert at the Bam HI site, and splicing and polyadenylation sites derived from the rabbit beta globin gene, which ensured proper processing of the transcribed insert in the cells. A pBR322 origin of replication and β-lactamase gene facilitated growth of the plasmid in E. coli. The plasmid conferred geneticin resistance through expression of the neomycin resistance gene under separate control of an HSV thymidine kinase promoter. The first transcription unit comprised a cytomegalovirus (CMV) promoter/enhancer upstream of a site for insertion of the cDNA sequences to be expressed, and splice and polyadenylation sites to ensure appropriate processing. The second transcription unit included a herpes simplex virus (HSV) thymidine kinase promoter/enhancer upstream of the neomycin resistance gene, allowing for selection of transfected cells in geneticin.

A wild-type p53 cDNA was inserted into pCMV-Neo-Bam to produce pC53-SN3. Similarly, a vector, pC53-SCX3, expressing a mutant cDNA from human colorectal tumor CX3, was also constructed. The only difference between pC53-SN3 and pC53-SCX3 was a single nucleotide (C to T) resulting in a substitution of alanine for valine at p53 codon 143 in pC53-SCX3. The two constructs were made as follows: a 1.8-kb Xba I fragment, extending from nucleotide –130 to 1671 relative to the translation initiation site, was isolated from wild-type or CX3 cDNA clones. The fragment was blunt-ended with the Klenow fragment of DNA polymerase, ligated to Bam HI linkers, and cloned into the unique Bam HI site in the expression vector pCMV-Neo-Bam.

The constructs were transfected into SW837 and SW480 cells (obtained from the American Type Culture Collection, Rockville, Md.), and geneticin-resistant colonies were counted 3 weeks later. Cells transfected with pC53-SN3 formed five-to tenfold fewer colonies than those transfected with pC53-SCX3 in both recipient cell types (Table 1).

TABLE 1

Colony formation after transfection with wild-type and mutant p53 expression vectors. For each experiment, one or two 75-cm² flasks were transfected, and the total colonies counted after 3 to 4 weeks of selection in geneticin (0.8 mg/ml). Exp. experiment.

| | | No. of geneticin-resistant colonies formed | |
|---|---|---|---|
| Cell line | Exp. | pC53-SCX3 (mutant) | pC53-SN3 (wild-type) |
| SW837 | 1 | 754 | 66 |
| | 2 | 817 | 62 |
| SW480 | 1 | 449 | 79 |
| | 2 | 364 | 26 |
| RK0 | 1 | 1858 | 190 |
| | 2 | 1825 | 166 |
| VAC0 235 | 1 | 18 | 16 |
| | 2 | 26 | 28 |

In both SW837 and SW480 cells, the number of colonies produced by the expression vector pCMV-Neo-Bam (without a p53 cDNA insert) was similar to that induced by the pC53-SCX3 construct.

Figure 6:
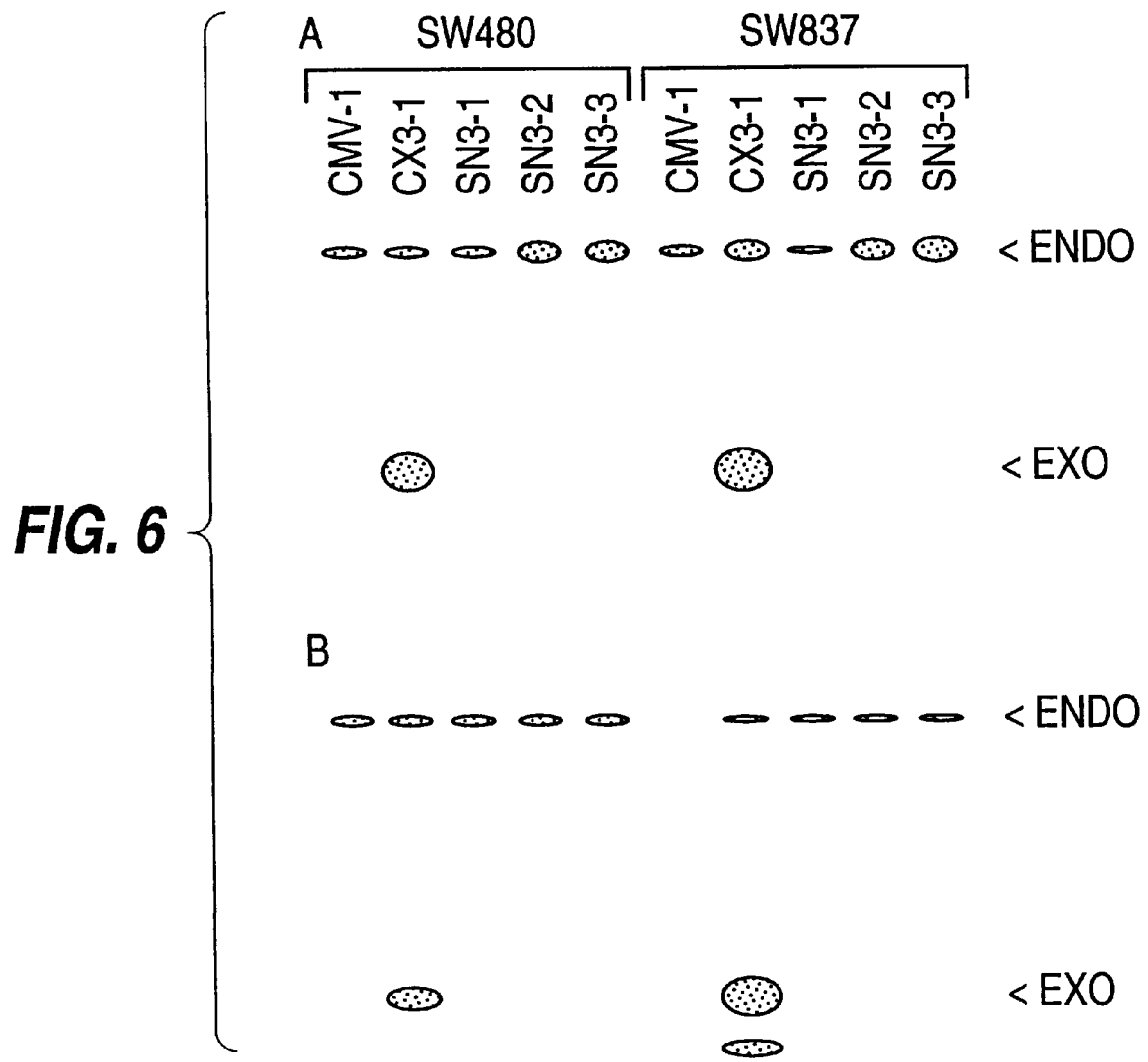
FIG. 6A shows RNase protection analysis of transfected clonal lines. A labeled antisense p53 probe was hybridized with total cellular RNA, and digested with RNase A. Endogenous RNA included all sequences represented in the labeled probe. Exogenous p53 RNA produced from the expression vectors extended only about ⅔ of the length of the probe.
FIG. 6B shows Southern blot analysis of transfected clonal lines. The exogenous p53 gene was present on a 1.8 kb BamHI fragment. The endogenous p53 gene gave rise to a 7.8 kb BamHI fragment. Other sized fragments presumably arose by rearrangements.

These results suggest that the wild-type p53 gene inhibits the clonal growth of both the SW837 and SW480 cell lines; however, a significant number of colonies formed after transfection of the wild-type construct. If wild-type p53 expression were truly inhibitory to cell growth, one would except that no colonies would form or that p53 expression in the colonies that did form would be reduced compared to that produced with the mutant p53 cDNA construct. To evaluate this issue, we expanded independent SW480 and SW837 colonies into lines, and ribonuclease (RNase) protection analysis was performed to determine the amount of p53 mRNA expressed from the exogenously introduced sequences. Twelve of 31 lines (38%) derived from transfection with the pC53-SCX3 construct were found to express the exogenous mutant p53 mRNA. This percentage was consistent with results expected in human cells transfected with a vector containing two independent transcription units. Previous studies have shown that, in contrast to rodent cells, primate cells are able to integrate only a small amount of foreign DNA (approximately 6 kb), so that only 10 to 30% of clones selected for the expression of one transcription unit also contain the second unit in an intact form (F. Collabere-Garapin, et al., Gene 50, 279 (1986); Hoeijmakers, et al., Exp. Cell Res., 169, 111 (1987); Mayne et al., Gene 66, 65 (1988), Dean, et al., Exp. Cell Res., 183, 473 (1989). In contrast, no expression of exogenous p53 wild-type mRNA was seen in any of 21 clonal lines established from either SW480 or SW837 cells transfected with the pC53-SN3 vector (FIG. 6A). These RNase protection results were supported by analysis of the exogenous p53 DNA sequences within the clones. All of the p53-expressing clones derived from the pC53-SCX3 transfection contained an intact copy of the exogenous p53 gene (FIG. 6B). In contrast, in all the clones derived from the pC53-SN3 transfection, the exogenous p53 sequences were deleted or rearranged (FIG. 6B).

Figure 7A:
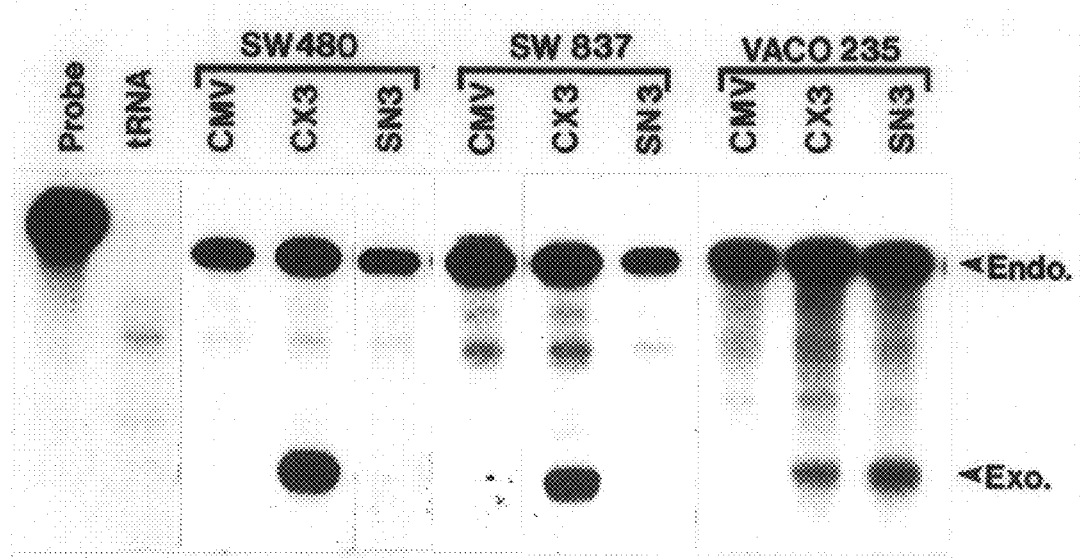
FIG. 7A shows expression analysis of pooled clones; the analysis was as described in FIG. 6A.
Figure 7B:
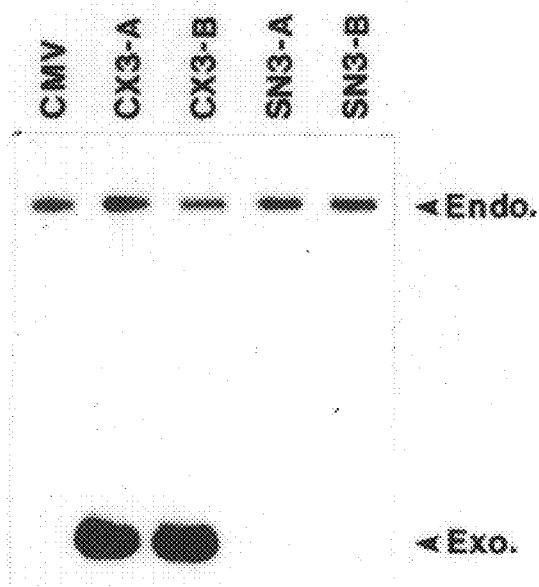
FIG. 7B shows a Southern blot analysis of SW480 pooled clones.

The results from individual clones were further supported by the analysis of pooled clones, in which numerous colonies could be simultaneously assessed. Forty or more clones from two to three separate transfection experiments were pooled and analyzed approximately 3 weeks after transfection. RNase protection studies showed substantial expression of wild-type sequences was not detectable (FIG. 7A). Results from Southern (DNA) blotting were consistent with the RNase protection studies, in that pooled colonies from the wild-type transfectants had no detectable unrearranged exogenous p53 sequences, in contrast to the intact p53 sequences in colonies derived from the mutant p53 cDNA expression vector (FIG. 7B).

The conclusions made from the above experiments are dependent on the assumption that p53 protein was produced in the transfected cell lines. Clones containing exogenous mutant p53 sequences produced p53 mRNA at a concentration 1.5 to 3.5 times higher than that produced by the endogenous p53 gene (FIGS. 6A and 7A). Immunoblot analysis showed that there was a concomitant small increase in p53 protein expression in the transfectants (1.5- to 3-fold) compared to the untransfected cells. However, this increase was difficult to measure quantitatively, since these cells produced significant amounts of endogenous p53 protein that (unlike endogenous p53 mRNA) could not be distinguished from that produced by the vectors. To confirm that transfected human cells expressed p53 protein from our constructs, we studied an additional colorectal carcinoma cell line (RKO). RKO cells were obtained through the generosity of M. Brattain. Although RKO cells did not contain a mutation within the susceptible p53 coding sequences, i.e., exons 5–9, they expressed low concentrations of p53 mRNA compared to normal colorectal mucosa or the other lines studied and did not produce detectable amounts of protein.

Results of colony formation assays in transfected RKO cells were similar to those in SW480 and SW837 cells. Colony formation by wild-type p53 gene transfectants occurred with a tenfold decrease in efficiency compared to the mutant p53 construct (Table 1). Immunocytochemical detection of p53 protein in transfected RKO cells was done as follows: approximately $5 \times 10^4$ cells were cytocentrifuged onto polylysine-coated slides, fixed for 10 min in formalin, and permeabilized for 5 min in 0.5% Triton X-100. A mouse monoclonal antibody against human p53 protein (Ab1801) in combination with the ABC immunoperoxidase system (Vector Laboratories), was used for immunocytochemical detection of p53 protein (Banks, et al., Eur. J. Biochem. 159, 529 (1986)). Ten to 20 randomly selected microscopic fields were analyzed per slide. These observations are consistent with the greater stability of mutant compared to wild-type p53 protein noted previously (C. A. Finlay et al., Mol. Cell Biol. 8, 531 (1988)). However, transient mRNA expression was also significantly lower in the SN3 transfectants compared to the SCX3 transfectants at 48 and 96 hours, supporting the idea that RKO cells expressing wild-type p53 were at a selective disadvantage compared to those producing mutant p53 products.

To obtain additional evidence that cells expressing p53 were inhibited in their growth potential, we examined the effect of p53 gene expression on DNA synthesis in transfected RKO cells were labeled with [$^3$H]thymidine for 2 hours. The cells were subsequently fixed, immunocytochemically stained for the presence of p53 protein, and autoradiographed. The number of cells undergoing DNA replication was only slightly lower in cells producing exogenous mutant p53 protein than in cells that did not express any detectable p53 protein. Expression of the wild-type protein, however, dramatically inhibited the incorporation of thymidine (Table 2).

TABLE 2

Immunocytochemistry and [$^3$H]thymidine incorporation of transfected RKO cells.

| Plasmid | Percent of cells expressing p53 protein at | | | | Percent of cells incorporating [$^3$H]thymidine in | |
|---|---|---|---|---|---|---|
| | 6 hrs | 24 hrs | 48 hrs | 96 hrs | p53 expressors | p53 non-expressors |
| pC53-SCX3 | 1.0 | 11 | 4.3 | 2.0 | 24 | 31 |
| pC53-SN3 | 1.9 | 5.2 | 0.3 | 0.2 | 1.7 | 33 |

These results all suggested that wild-type p53 exerted an inhibitory effect on the growth of carcinoma cells in vitro. To evaluate whether this inhibitory effect was cell type-specific, we transfected colorectal epithelial cells derived from a benign tumor of the colon (the VACO 235 adenoma cell line). VACO 235 cells are described by J. K. V. Willson et al., Cancer Res., 47, 2704 (1987). Previous studies have shown that most adenomas contain two copies of chromosome 17p and express wild-type p53 mRNA at concentrations similar to that of normal colonic mucosa. Analogously, the p53 alleles of the VACO 235 cell line were sequenced (exons 5–9) and found to be wild-type and the expression of p53 mRNA was found to be similar to that of normal colorectal mucosa. In contrast to the results seen with SW480, SW837, and RKO cells, the pC53-SN3 and pC53-SCX3 constructs produced similar numbers of geneticin-resistant colonies after transfection of the VACO 235 line (Table 1). We considered, however, that the most definitive test for differential growth inhibition by wild-type versus mutant p53 genes involved analysis of exogenous p53 expression in pooled transfectants. Through such analysis, a large number of colonies could be examined simultaneously and the expression of exogenous mutant and wild-type p53 genes directly compared. Striking differences in the relative expression from the transfected genes were seen in all three carcinoma cell lines tested. VACO 235 transfectants, however, expressed similar amounts of exogenous p53 mRNA from either pC53-SN3 (wild-type) or pC53-SCX3 (mutant) p53 constructs (FIG. 7A).

In summary, our results suggest that expression of the wild-type p53 gene in colorectal carcinoma cell lines was incompatible with proliferation. The inhibitor effects of wild-type p53 were specific in two ways. First, a single point mutation in a p53 gene construct abrogated its suppressive properties as measured by three separate assays (colony formation, exogenous p53 expression in transfected clones, and thymidine incorporation). The CX3 mutant provided a control for gene specificity as it contained only one conservative mutation, resulting in a substitution of one hydrophobic amino acid (alanine) for another (valine) at a single codon. Second, the growth-suppressive effect of the wild-type p53 construct was cell type-specific. Introduction of the wild-type vector into the VACO 235 adenoma cell line had no measurable inhibitory effect compared to the mutant p53 vector. There are several differences between the cell lines that could account for the differential effect of the introduced vectors. Regardless of the basis for the difference, the results with the VACO 235 cell line minimize the possibility that the wild-type p53 construct had some nonspecific, toxic effect on recipient cells; the effect was cell type-dependent.

The transfection and expression results of Table 1 and FIG. 7A suggest that cells at the premalignant stages of tumor progression (VACO 235) may be less sensitive to the inhibitory effects of wild-type p53 than malignant cells (SW480, SW837, and RKO). This hypothesis is consistent with previous results that suggest the wild-type p53 is less inhibitory to the growth of normal rat embryo fibroblasts than to their oncogene-transfected derivatives. Finlay et al., Cell 57, 1083 (1989); Eliyahu et al., Proc. Natl. Acad. Sci. USA, 86, 8763 (1989). This sensitivity may only be relative: expression of the wild-type gene at high concentrations might inhibit the growth of any cell type, including non-neoplastic cells, by overwhelming normal regulatory processes such as phosphorylation. Samad et al., Proc. Natl. Acad. Sci. USA, 83, 897 (1986); Meek et al., Mol. Cell Biol. 8, 461 (1988). Genetic alterations that occur during the progression of colorectal tumors may increase the sensitivity of cells to p53 inhibition, making wild-type p53 expression a key, rate-limiting factor for further tumor growth and expansion. At this point, and not before, mutations in the p53 gene would confer a selective growth advantage to cells in vivo, which would explain the frequent occurrence of p53 gene mutations and allelic loss only in the more advanced stages of colorectal tumorigenesis.

Example 8

This example demonstrates the identification of human genomic fragments that can bond to wt p53 protein in vitro.

Figure 8A:
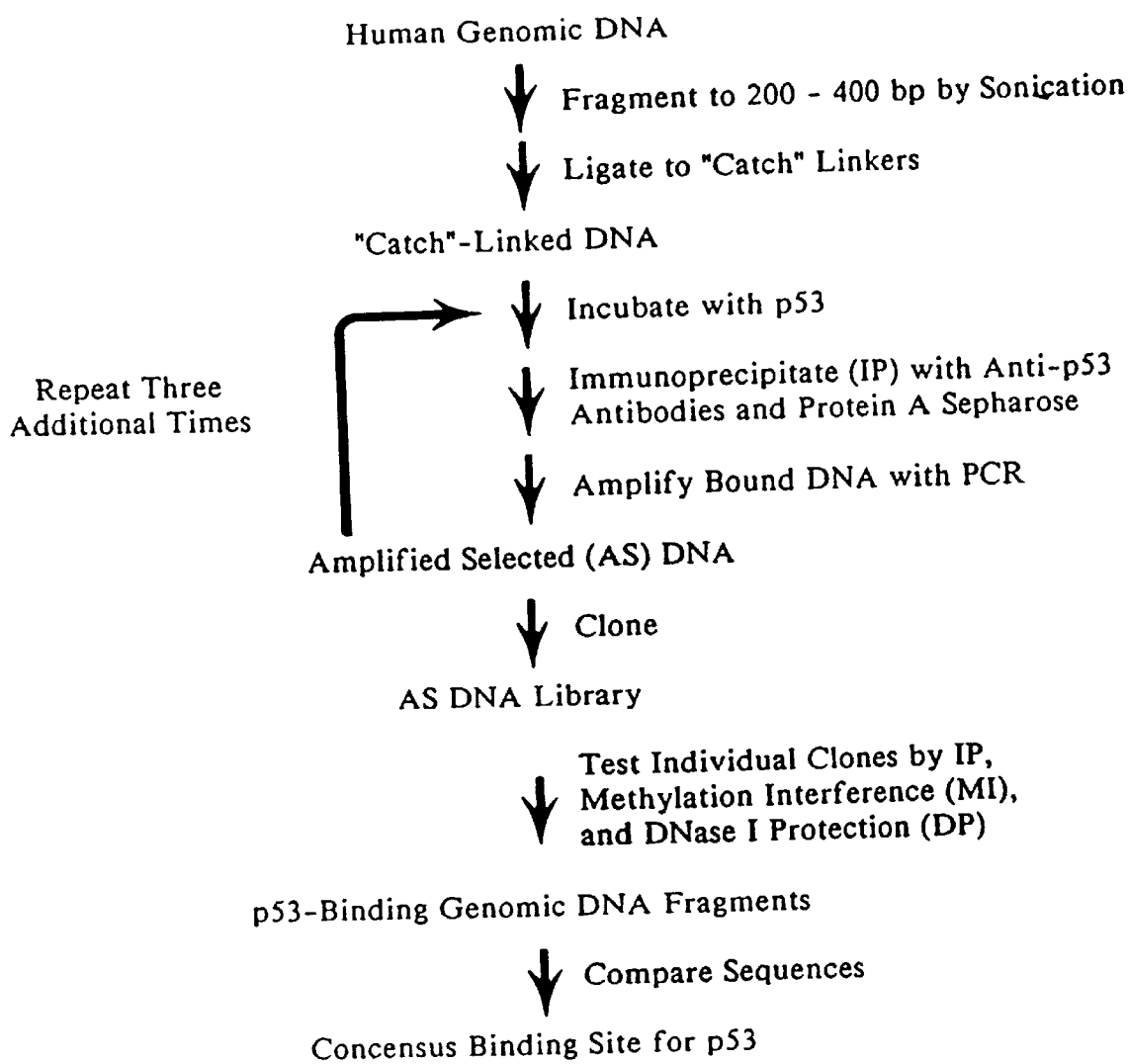
FIG. 8A. Experimental strategy used for isolation and analysis of human genomic DNA fragments which bound to p53.

This schema in FIG. 8A outlines the experimental strategy used for the isolation and analysis of p53 binding sites. Total human genomic DNA fragments were ligated to specially designed "catch" linkers (Kinzler, et al. (1989), *Nucleic Acids Research,* 17:3645–3653, and Kinzler, et al. (1990), *Molec. Cell. Biol.,* 10:634–642) to allow for subsequent PCR amplification and cloning. The linked genomic DNA was then incubated with wt p53 and precipitated with anti-p53 antibodies. The bound DNA was subsequently amplified by PCR using primers complementary to the catch linkers, and the process repeated. After four rounds of sequential immunoprecipitation and PCR, the amplified and selected (AS) DNA was cloned. Clones were picked at random and tested for p53 binding first by immunoprecipitation (IP), and then by methylation interference (MI) and DNase I protection (DP).

Following the outline in FIG. 8A., we tested the inserts of 530 clones for binding to p53. Restriction fragments of the clones were end-labeled and incubated with purified human wt p53 protein produced in baculovirus-infected cells.

Whole-genome PCR was performed as previously described, except that only one oligonucleotide (5'-GAGTAGAATTCTAATATCTC-3') (SEQ ID NO:37) was used for amplification (Kinzler, et al. (1989), *Nucleic Acids Research,* 17:3645–3653, and Kinzler, et al. (1990), *Molec. Cell. Biol.,* 10:634–642). Two hundred ng of "catch"-linked human genomic DNA were incubated with 100 ng of baculovirus-produced human wt p53 purified as described (Friedman, et al. (1990), *Proc. Natl. Acad. Sci.* U.S.A., 87:9275–9279), and immunoprecipitated as described below. After 4 rounds of IP and PCR, the AS DNA was cleaved with Eco RI and cloned into either the vector Lambda Zap II or pBluescript II SK+ (Stratagene). Individual clones were picked at random and tested for p53 binding. In panel B, cloned plasmid DNA samples were cleaved with Eco RI and end-labeled by Klenow fill-in. For IP (McKay, et al. (1981), *J. Mol. Biol,* 145:471–479), ten ng of DNA were incubated with 100 ng of baculovirus-produced human wt p53 and 100 ng of poly dI-dC at 4° C. for 30 minutes in 100 µl of "DNA-binding buffer" containing 100 mM NaCl, 20 mM Tris, pH 7.0, 10% glycerol, 1% NP40, and 5 mM DTT. DNA fragments bound to p53 were complexed to antibodies by the addition of 8 µl containing 400 ng each of anti-p53 antibodies pAb421 and pAb1801, both obtained from Oncogene Science, and incubated for 30 minutes at 4° C. The DNA-binding buffer containing 1.5 mg protein A precipitated following the addition of 26 µl of DNA-binding buffer containing 1.5 mg protein A Sepharose and 10 µg of poly dI-dC and mixing at 4° C. for 30 minutes. After removal of the supernatant, the immunoprecipitate was washed twice with 1 ml of DNA-binding buffer. Bound DNA was purified by treatment with SDS and proteinase K at 48° C. for 30 minutes, extracted with phenol and chloroform, precipitated with ethanol, separated by electrophoresis on a 10% nondenaturing polyacrylamide gel, and autoradiographed.

Twenty-three of the clones were found to contain fragments that bound to p53. Examples of the IP experiments are shown in FIG. 8B. Clone S61 (lanes 11B,C) contains a single genomic fragment of 202 bp which bound to p53. Clone N2 contained five fragments, only one of which (357 bp) bound to p53 (lanes 10B,C). Other examples of p53-binding fragments were obtained, and each of these was subcloned for further analysis. In contrast, we found that none of over 1000 clones containing unselected human DNA inserts of similar size bound to p53 using the IP assay. Thus, the whole-genome PCR procedure significant enriched for p53-binding sequences.

Example 9

This example demonstrates the localization of p53 contacts with bound DNA fragments.

Localization of the regions bound by p53 was obtained by DP or MI assays using the subcloned DNA fragments as probes. For MI, the fragments were methylated at G residues and bound to p53 (FIG. 9). methylation of G residues critical for p53 binding resulted in interference with IP. For example, methylation at nucleotides, 217, 22, 227 to 229, and 233 of the 248 bp insert from clone 11B3 completely interfered with the binding of this fragment to p53 (FIG. 9, footprint 2). When the opposite strand was analyzed, interference was observed at the G residues corresponding to nucleotides 219, 223, 224, 230, 235, and 236 (FIG. 9, footprint 1). For DP, labelled DNA fragments were first subject to IP, then incubated with various amounts of DNase I. For clone N22, p53 binding provided protection against DNase I cleavage at residues 187 to 211 (FIG. 9, footprint 9). MI showed interference by G residues only within the region protected by DNase I (FIG. 9, footprint 10). Other examples of DP and MI mapping are shown in FIG. 9. p53-binding DNA fragments were subcloned and labeled on one end, gel-purified and subjected to DP or MI mapping. For MI, 10 ng of DNA were incubated in 200 µl of 50 mM Na-cacodylate, 1 mM EDTA, pH 8.0 and 5 µl of 10% dimethylsulfate/90% ethanol for 5 minutes at 20° C. to methylate G residues. Fifty µl containing 1.5 m Na-Acetate, 1 M β-mercaptoethanol and 60 µg of glycogen were added. The mixture was ethanol-precipitated, washed, and resuspended in 5 µl of 3 mM Tris, 0.2 mM EDTA, pH 7.5, and allowed to bind to wild-type p53 as described in the legend to FIG. 1. After IP and DNA purification, the samples were incubated with 100 µl of 1 M piperidine at 90° C. for 30 minutes. The samples were then dried under vacuum and separated electrophoretically on a 6% polyacrylamide sequencing gel. The control DNA samples were carried through all incubations except no p53 was added. For these control samples, the protein A Sepharose pellets were treated with SDS and proteinase K without removal of the supernatants (which contained the labeled DNA in the absence of p53).

For DP assays, end-labeled DNA fragments were immunoprecipitated as described in the legend to FIG. 8. The protein A Sepharose pellets were incubated for two minutes at 25° C. with 200 ng DNase I in 5 mM MgCl$_2$. After purification of the DNA, as described above, samples were separated by electrophoresis on sequencing gels and loaded as described above for MI. MI was performed on all 18 genomic DNA fragments which bound to p53. DP assays were performed on 13 fragments and the regions of protection uniformly coincided with those indicated by the MI assays.

Example 10

This example analyzes the sequences of p53-bound DNA regions.

We next compared the sequences of the twenty-three clones. The average insert sequence was 307 bp (range 139–470). We found that ten of the twenty-three clones were not unique, showing at least one hundred contiguous nucleotides identical to one other clone. Thus, the twenty-three clones represented only eighteen independent genomic DNA fragments. We attempted to find similarities among these eighteen fragments by computer methods, but found no significant relationships. However, when we aligned the regions involved in p53 binding (as assessed by MI and DP), a striking and consistent feature of the clones became apparent (FIG. 10). Each of the binding sites contained two copies of the 10 bp motif 5'-RRRCWWGYYY-3' (SEQ ID NO:3) separated by 0 to 13 bp. One clone (S592) contained two separate areas of footprinting, and both regions contained a dimer of the 10 bp motif (FIG. 10). In all clones, the regions displaying DP and MI were always centered within the dimers, and G residues within the 10 bp motif strongly interfered with binding to p53 (examples in FIG. 9). The 10 bp consensus monomer contained an internal symmetry, with two oppositely oriented half-sites of the form 5'-RRRCW-3'. This symmetry was extended in the dimers, which contained four half-sites oriented in alternating directions, forming a pseudopalindromic structure, sometimes with an intervening loop. This consensus dimer was also recognized in the p53 binding sequence mapped within plasmid CBE10d (FIG. 10). Despite the remarkable symmetry noted for all p53 binding sequences, none of the genomic sites were palindromic.

Example 11

This example demonstrates that a dimer of the consensus motif is required to bind p53 and that mutant p53 proteins found in tumors do not bind to the consensus sequence.

To determine if the 10 bp consensus monomer could bind to p53, a synthetic oligonucleotide (5'-AGGCATGTCT-3') (SEQ ID NO:38) containing the consensus sequence was studied. Oligonucleotide duplexes were tested either directly or after cloning into plasmid vectors. The monomer was found not to bind to p53, either alone (not shown) or flanked by 43 nucleotides of plasmid sequences (FIG. 11A, lane 5). In contrast, the dimers (composed of two copies of the monomer arranged in head-to-head, tail-to-tail, or head-to-tail orientation), each bound strongly to p53 protein (FIG. 11A, lanes 1 to 4, 6). Higher-order oligomers of the monomer did not bind any better than the dimer in the IP assay (FIG. 11A, lanes 6 to 8). A different monomer, still fitting the consensus sequence, but perfectly palindromic, also bound as a dimer but not as a monomer (FIG. 10, synthetic oligonucleotides 3,4). Two variants of the consensus motif were also tested for binding. In the first, the two critical G:C bp's at position 4 and 6 of the monomer were substituted with A:T bp's (FIG. 10, synthetic oligonucleotides 1,2). Although this sequence was perfectly symmetrical, it did not bind to p53 either as a monomer or as a dimer. We also tested direct repeats of the 5'-PuPuPuC(A/T)-3' (SEQ ID NO:39) half-site, and found that these did not bind to p53 (FIG. 10, synthetic oligonucleotide 5). Thus, the mirror-image symmetry of the half-sites within the 10 bp consensus monomer was critical for its activity.

Finally, we tested p53 mutants representing each of the four "hot-spots" frequently altered in human cancers ((Nigro, et al. (1989), Nature, 342:705–708, and Holstein, et al. (1991), Science, 253:49–53) for ability to bind to the consensus dimer. None of the p53 mutants bound appreciably to this sequence (FIG. 11B) under conditions where the wt protein bound strongly. These experiments also shows that in vitro translated p53, as well as that purified from baculovirus-infected insect cells, had the capacity to bind DNA specifically.

In summary, a set of human genomic DNA sequences which could bind p53 were isolated and used to define a consensus binding sequence for p53. The symmetry of the four half-sites within the consensus dimers suggests that p53 interacts with DNA as a tetrameric protein. This is consistent with studies suggesting that p53 assembles into homotetramers (Krais, et al. (1988), J. Virol., 62:4737–4744, and Weinberg (1991), Science, 254:1138–1146).

Example 12

This example demonstrates that intact p53 can activate expression in human cells.

We first made reporter plasmids (PG$_n$-CAT series) containing part of the polyomavirus early promoter and the CAT gene located downstream of DNA sequences which could bind to p53 in vitro (FIG. 8). For the CAT reporters, concatemers of the p53-binding region of C$_{BE}$ were formed by ligation of complementary oligonucleotides, ligated into the EcoRV site of pBluescript II SK+ (Stratagene) to form the PG$_n$ and MG$_n$ series. The BglII-BamHI fragment of pPyO1CAT (Murakami, et al. (1990) Oncogene, 5:5), containing the polyomavirus early promoter and the CAT gene coding region, was ligated into the BamHI site of the $PG_n$ and $MG_n$ series clones to form the $PG_n$-CAT and $MG_n$-CAT series, and the orientation of the inserts characterized by restriction enzyme analysis. The $PG_9$-$MG_n$-CAT and $PG_{13}$-$MG_n$-CAT series were formed by excising the HindIII-SalI fragments of $PG_9$-CAT and $PG_{13}$-CAT, blunt-ending, attaching XbaI linkers, and ligating into the XbaI site of the $MG_n$-CAT series plasmids (where n=1, 5, 10, and 15). For the yeast β-galactosidase reporter plasmids, PG and MG sequences were ligated as SalI-SmaI fragments to the SalI and filled-in XhoI sites of pCZ (Buchanan, et al. (1988), *Mol. Cell Biol.*, 8:50806). The construction of the p53-wt expression construct has been described (Baker, et al. (1990), *Science*, 249:912); the mutant expression plasmids were constructed similarly from the previously described cDNA plasmids (Nigro, et al. (1989), *Nature*, 342:705, and Kern, et al. (1991), *Oncogene*, 6:131), or in the case of the engineered phosphorylation site mutants, by in vitro mutagenesis (Altered Sites, Promega) with verification by sequencing. The construction of the yeast p53 expression vectors based on pRS314 has been described (Nigro, et al., *Mol. Cell Biol.* (in press)).

Figure 12B:
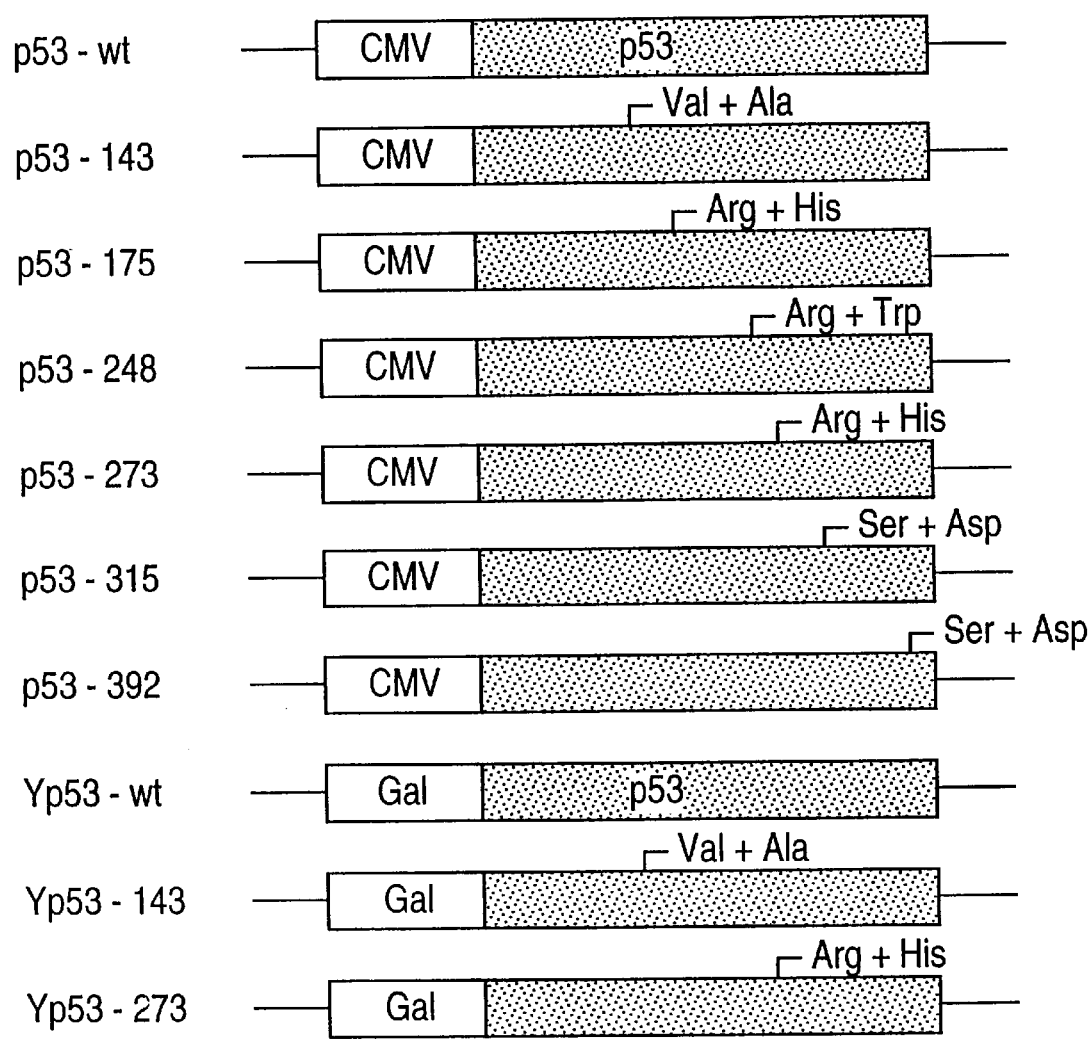
FIG. 12B. Expression vectors. CMV, the cytomegalovirus promoter from the parent vector pCMVneoBam. Gal, the galactose-inducible promoter from yeast.

For the p53 binding sequences, we used a series of concatemers of the oligonucleotide PG (5'-CCTGCCTGGACTTGCCTGG-3') (SEQ ID NO:40). This contained the binding region of plasmid $C_{BE}$, previously shown to bind p53 in vitro. The reporter and an expression vector coding for the intact human wild-type protein (p53-wt) (FIG. 12B), were transfected together into the human colorectal cancer cell line HCT 116. This line makes low amounts of apparently wild-type p53 protein.

Exons 5–8 of the p53 genes from HCT 116 cells were amplified by PCR and sequenced as described in Sidransky et al. (1991), *Science*, 252:706. Previously, these exons had been shown to contain over 90% of the mutations observed in human tumors. No mutations were observed from HCT 116 cells. Small amounts of apparently wild-type protein could be detected in Western blots of HCT 116 protein (See FIG. 16B).

Figure 13A:
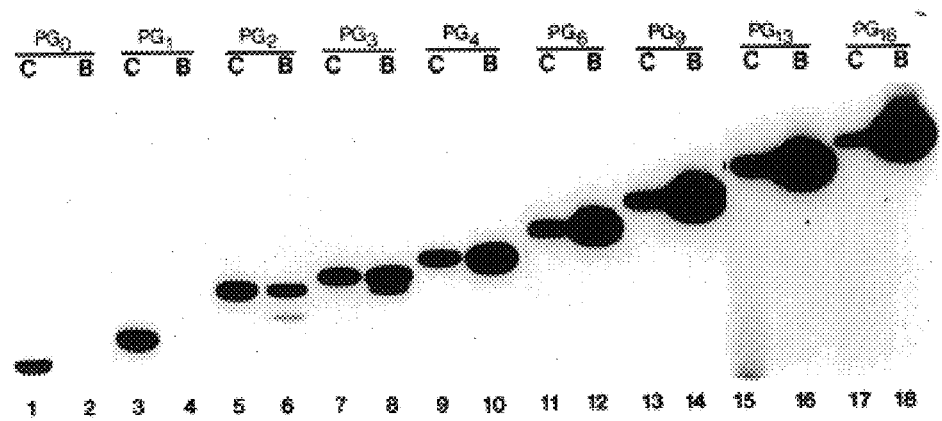
FIG. 13A. Relative DNA-binding abilities of various length concatemers of a p53-binding sequence ($PG_n$ series), using an immunoprecipitation assay. Clones were cleaved by restriction endonucleases to extricate the concatemers, end-labelled, incubated with purified baculovirus-produced wild-type human p53, immunoprecipitated with anti-p53 and protein A-Sepharose, and bound fragments recovered and separated on a nondenaturing polyacrylamide gel. C, control lane, containing 2% of the labeled DNA used in the binding reactions. B, bound DNA recovered from the binding reactions.
Figure 13B:
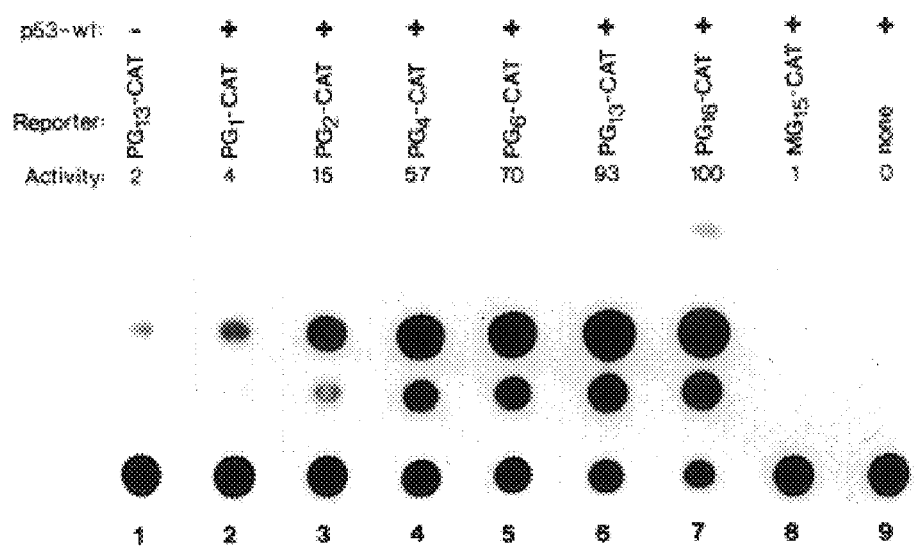
FIG. 13B. Transactivation efficiencies of reporters containing the various $PG_n$ concatemers compared by chloramphenicol acetyltransferase (CAT) assay. 1.7 µg of the expression vector p53-wt were transfected into HCT 116 cells. Reporters had one orientation of the $PG_n$ sequence ( . . . TGCCT . . . Py . . . CAT . . . ), except for $PG_2$-CAT and $PG_{13}$-CAT, which had the opposite orientation ( . . . AGGCA . . . Py . . . CAT . . . ). Results are expressed relative to the CAT activity in lane 7, which was arbitrarily set at 100.

The intact wild-type p53 protein was indeed able to activate transcription (FIG. 13). We found that the level of transactivation of the CAT gene depended on the strength of binding to p53 of the upstream sequences. Thus, the longer the number of PG repeats, the greater the binding to p53 in vitro (FIG. 13A) and the higher the CAT expression in vivo (FIG. 13B, lanes 1–7). The level of transactivation also increased with the amount of p53 expression vector transfected (Table 3).

TABLE 3

| p53 Expression Vector[2/] | Reporter | Relative CAT Activity[1/] | | | |
|---|---|---|---|---|---|
| | | | Exp. 2 | | |
| | | Exp. 1 | .85 μg | 2.55 μg | Exp. 3 |
| p53-wt | PG$_{13}$CAT | 100 | 100 | 210 | 100 |
| | Tumor-derived mutations: | | | | |
| p53-143 | PG$_{13}$CAT | 3 | 1 | 4 | |
| p53-175 | PG$_{13}$CAT | 2 | 3 | 6 | |
| p53-248 | PG$_{13}$CAT | 2 | 4 | 7 | |
| p53-273 | PG$_{13}$CAT | 2 | 2 | 3 | |

TABLE 3-continued

| p53 Expression Vector[2/] | Reporter | Relative CAT Activity[1/] | | | |
|---|---|---|---|---|---|
| | | | Exp. 2 | | |
| | | Exp. 1 | .85 μg | 2.55 μg | Exp. 3 |
| | Endogenous activities: | | | | |
| p53-wt | MG$_{15}$CAT[3/] | | <1 | | 2 |
| none[4/] | PG$_{13}$CAT | | 20 | | 2 |

[1/]All transfections used 1.7 μg reporter in HCT 116 cells. Transfection and CAT assays were performed as described (Sadransky, et al. (1991), Science, 252: 706). Activities reflect the fraction of chloramphenicol converted to an acetylated form, expressed as relative values with one transfection of each experiment arbitrarily designated as having a value of 100. Three representative experiments (Exp.) shown.
[2/]Experiment 2 used both 0.85 and 2.55 μg levels of expressor. Experiment 1 used 1.7 μg, and experiment 3 used 0.85 μg.
[3/]MG$_{15}$-CAT provided a control for DNA-binding specificity and an estimate of background from promoter-independent "readthrough" transcription and/or basal promoter activity.
[4/]The expressor-negative transfection provided an estimate of the activity from endogenous wild-type p53 of the HCT 116 cells. In various transfections, the endogenous activity was 2–20% of that following transfection with exogenous wild-type p53, depending on the efficiency of transfection. The activity from endogenous p53 was diminished by transfection of oncogenic mutant p53.

Figure 15A:
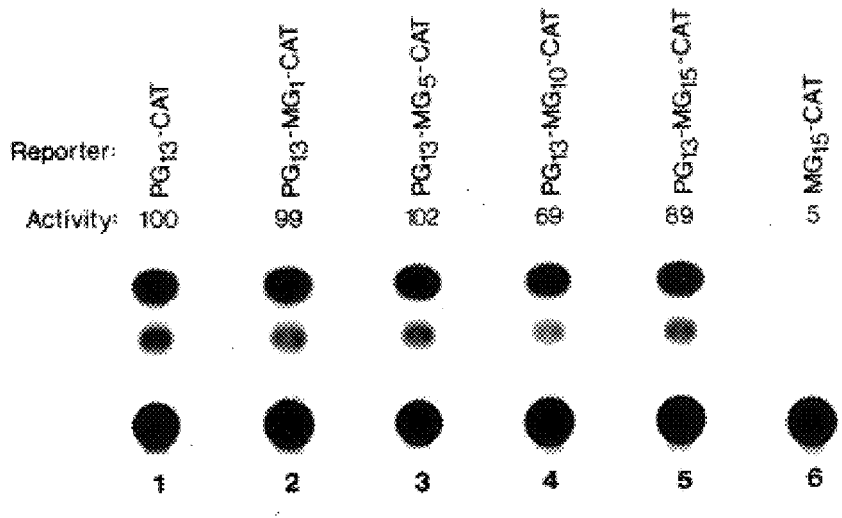
FIG. 15A. Efficiencies of reporters with $PG_{13}$ separated by varying distances from the polyomavirus promoter. Various lengths of the non-binding sequence ($MG_n$ series) were used to provide inert spacers of defined length (see FIG. 8A). CAT assays are shown.
Figure 15B:
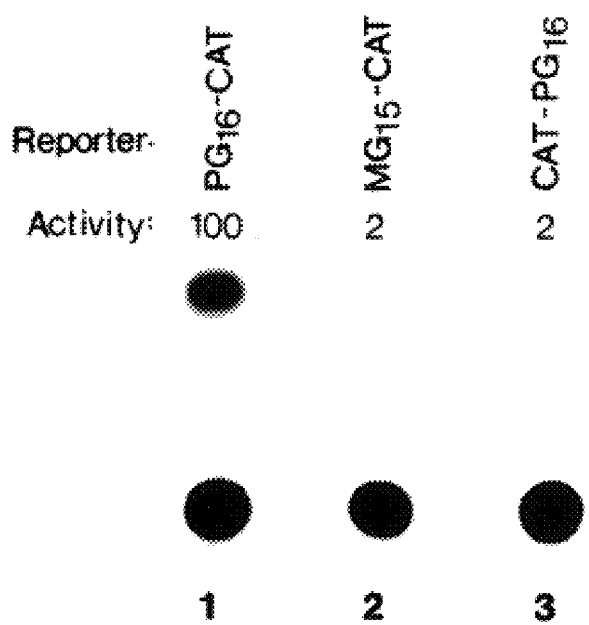
FIG. 15B. Transactivation efficiency of a reporter with $PG_{16}$ downstream of CAT (CAT-$PG_{16}$). 1.7 µg each of expression and reporter construct were transfected. The $MG_{15}$-CAT served as a negative control. CAT assays are shown.

Specificity for the binding sequences was tested by replacing six GC basepairs in the 18-basepair oligonucleotide to generate a mutant form of PG, termed MG (5'-CCTTAATGGACTTTAATGG-3') (SEQ ID NO:41). This sequence, when multimerized and placed upstream of the CAT reporter, did not bind to p53 in vitro (FIG. 14, lanes 7 and 8), nor did it activate CAT expression in vivo (Table 3; FIG. 13B, lane 8; FIG. 15A, lane 6, FIG. 15B, lane 2). The transactivation of CAT was independent of the orientation of the PG multimer upstream of the CAT gene (FIG. 13B). Placing an additional 59 to 333 basepairs between the PG multimer and the promoter also had little effect on transactivation (FIG. 15A, lanes 2–5). However, placement of the PG binding sequences downstream of the CAT gene did not allow transactivation (FIG. 15, lane 3). These observations indicated that the PG sequences act as an upstream activator element, although not as a classical enhancer.

CAT assay. Cultures of HCT 116 cells at 50–80% confluence in 25 cm² flasks were transfected using Lipofectin (BRL, Gaithersburg, Md.) according to the manufacturer's instructions. All flasks within an experiment were transfected with the same total amount of plasmid using pCM-VneoBam or pBluescript II SK+ as "filler". Cells were harvested at 20–24 hr. and the CAT activity of the lysates measured by acetylation of $^{14}$C-labeled chloramphenicol (ICN) as previously described (Gorman, et al. (1982), *Mol. Cell Biol.*, 2:1044). The Bio-Rad protein assay was used to assure equivalence of lysate protein. Percent conversion to the acetylated form of chloramphenicol was calculated after quantitation by scintillation counting of excised chromatographic spots. Results reported are representative of at least two transfections done on separate days.

Example 13

This example demonstrates that oncogenic mutant p53 genes consistently fail to transactivate.

Figure 16A:
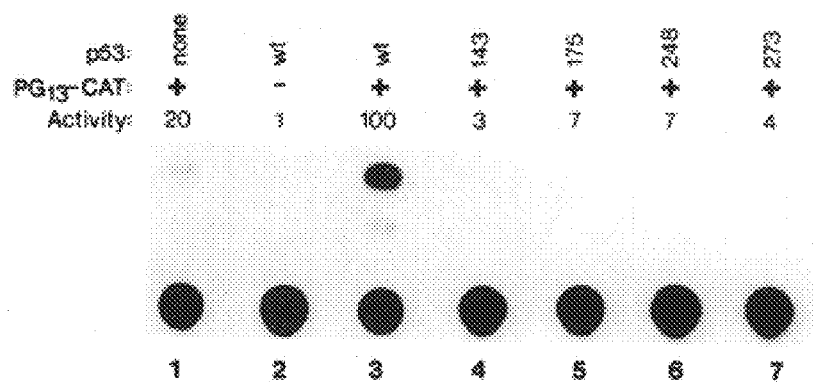
FIG. 16A. Representative CAT assays (Exp. 2 from Table 1).
Figure 16B:
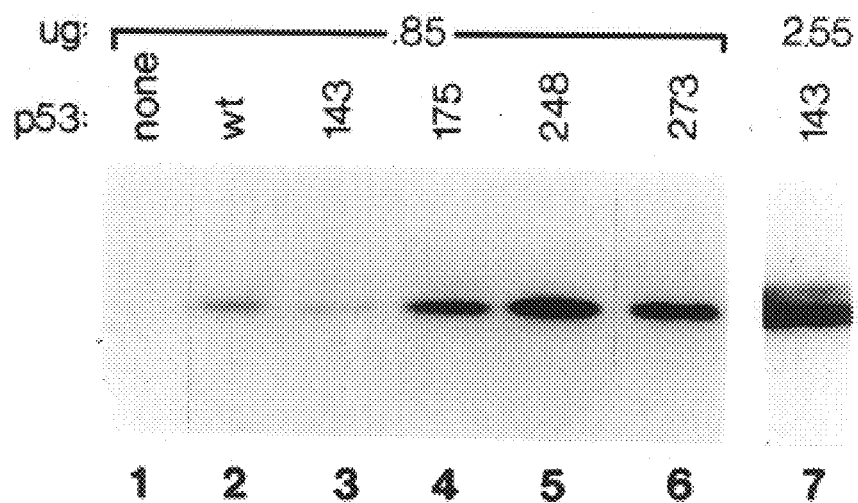
FIG. 16B. Western blot analysis of p53 expression in lysates of transfected cells, showing levels of expression at least as high as that of wild-type p53 were obtained with the mutant p53 clones. In one case ($143^{ala}$), the level of expression of p53 (lane 3) was slightly lower than with the other constructs, for unknown reasons. When 2.55 µg of vector was used in the transfection, however, the level produced by the p53-143 vector (lane 7) was at least as high as that for the p53-wt vector, but not transactivation was observed (Table I).

The precise correlation between the binding of the PG multimer in vitro (FIG. 13A) and the expression from PG$_n$-CAT reporters in vivo (FIG. 13B) strongly suggested that this expression was a direct result of p53 binding to PG multimers in vivo. If such an activity of p53 were crucial to its tumor suppressor activity, one would expect that naturally occurring mutants of p53 would be defective in this function. p53 mutations generally occur in four different p53 "hot-spot" regions, representing four evolutionarily conserved domains of the p53 protein (Baker, et al. (1989), *Science*, 244:217, Hollstein, et al. (1991), *Science*, 253:49, and Soussi, et al. (1987), *Oncogene*, 1:71). Mutant p53 genes representing each of these hot-spots were transiently transfected into cells together with the PG$_{13}$-CAT reporter plasmid. The consistency of the results obtained with these mutant expression vectors was striking. All tumor-derived mutations examined had lost the ability to transactivate CAT, despite the wide range of positions (codons 143–273) in which these mutations were situated (Table 3, and FIG. 16A). As might be expected for a cell line expressing low amounts of endogenous wild-type p53, there was often some innate transactivating ability associated with the HCT 116 cells themselves (Table 3; FIG. 13B, lane 1; FIG. 16A, lane 1); interestingly, the levels of CAT observed with the mutants (Table 3 and FIG. 16A, lanes 4–7) were actually less than that observed with no exogenous p53 expression vector, suggesting that the mutant p53 products might be inhibiting the low amounts of expression mediated by the endogenous p53 (discussed below). The mutants studied included one which was typical of those found in the germline of Li-Fraumeni patients (248$^{trp}$)(Malkin, et al. (1990), *Science*, 250:1233; Strivastava, et al. (1990), *Nature*, 348:747) and three found commonly in a variety of human tumors 9143$^{val}$, 175$^{his}$, 273$^{his}$)(Hollstein, et al. (1991), *Science*, 253:49). Immunoblots confirmed that mutant p53 proteins were expressed at levels comparable to those of wild-type p53 (FIG. 16B).

Western blots were performed as follows: 100 $\mu$g protein of each cell lysate was separated on a 10% polyacrylamide SDS gel, transferred onto a PVDF (Millipore, Bedford, Mass.) membrane, blocked with 5% nonfat milk, incubated with 1 $\mu$g/ml PAb1801 (Oncogene Sciences) then $^{125}$I-labeled goat-anti-mouse Ab (NEN), and autoradiographed. The inability of p53 proteins having tumor-derived mutations to bind specifically to the p53 recognition sequences in this construct (FIG. 14, lanes 3–6) is thus consistently reflected as defects in transactivation.

Example 14

This example demonstrates that intact p53 transactivates in yeast.

We next sought to determine whether this activity of p53 was confined to mammalian cells. If the ability of p53 to bind to DNA sequences in vivo and activate the transcription of adjacent genes were an intrinsic feature of the protein, it was possible that this activity would be manifest in simpler eukaryotes. Indeed, the N-terminal acidic activation domain of p53 has been reported to function in *S. cerevisiae* when fused to the DNA-binding domain of GAL4 (Fields, et al. (1990), *Science*, 249:1046). We thus stably transfected yeast with the LacZ reporter gene placed downstream of PG multimers (PG$_n$-LacZ), as well as with a galactose-inducible p53 expression vector (FIG. 12). The addition of galactose to the medium resulted in p53 expression accompanied by a dramatic elevation in $\beta$-galactosidase expression (Table 4). When the MG multimer (non-p53 binding) was substituted for the PG multimer, no activation was observed (Table 4). Moreover, p53 mutants had no capacity to transactivate in yeast cells (Table 4). Thus, the results in *S. cerevisiae* were analogous to those observed in human cells.

TABLE 4

Activation of Gene Expression in Yeast by p53

| p53 Expression Vector | Reporter | $\beta$-Gal Activity | |
|---|---|---|---|
| | | Exp. 1 | Exp. 2 |
| none | PG16-LacZ | 3 | 2 |
| Yp53 | PG16-LacZ | 13,000 | 8,000 |
| Yp53-143 | PG16-LacZ | 150 | 85 |
| Yp53-273 | PG16-LacZ | 5 | 2 |
| Yp53 | PG4-LacZ | 15,000 | 11,000 |
| Yp53 | PG1-LacZ | 2,600 | 3,000 |
| Yp53 | MG15-LacZ | 15 | 4 |

Wild-type or mutant p53 expression vectors and the $\beta$-galactosidase reporter plasmids were transfected into *S. cerevisiae* and clones obtained. p53 expression was induced with galactose, and $\beta$-galactosidase activity was measured in units of nanomoles per minute per milligram of protein. Two independent clones (Exp. 1 and Exp. 2) were tested. Less than 1 unit was seen in the absence of galactose induction. The residual activity of the Yp53-143 mutant may have been due to a slight wild-type activity observable with valine to alanine substitution mutants at the relatively low temperature (30° C.) used for yeast growth.

Example 15

This example demonstrates the dominant-negative effect of p53 mutations on wild-type p53's ability to bind DNA and enhance transcription.

Figure 17:
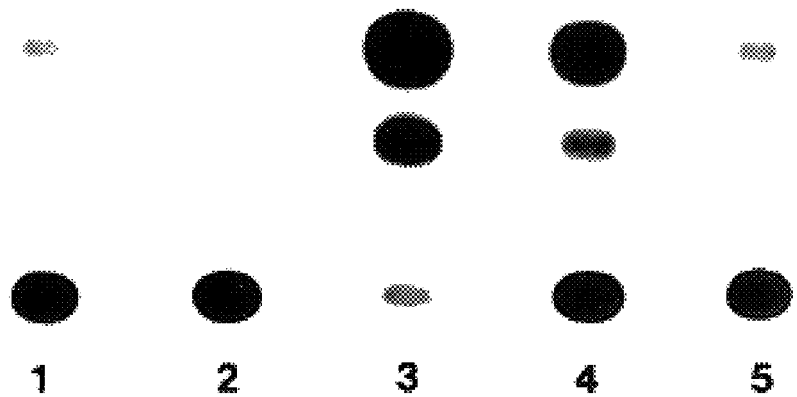
FIG. 17. Effect of co-expressed 175$^{his}$ mutant p53 on transactivation by wild-type p53 is shown. 1.7 μg of PG$_{13}$-CAT reporter was used with the stated amounts of p53 expression constructs. The balance of transfected plasmid was pCMVneoBam (for expressor) and pBluescript II SK+ (for reporter) to a total of 5.1 μg. CAT assays are shown.
Figure 18:
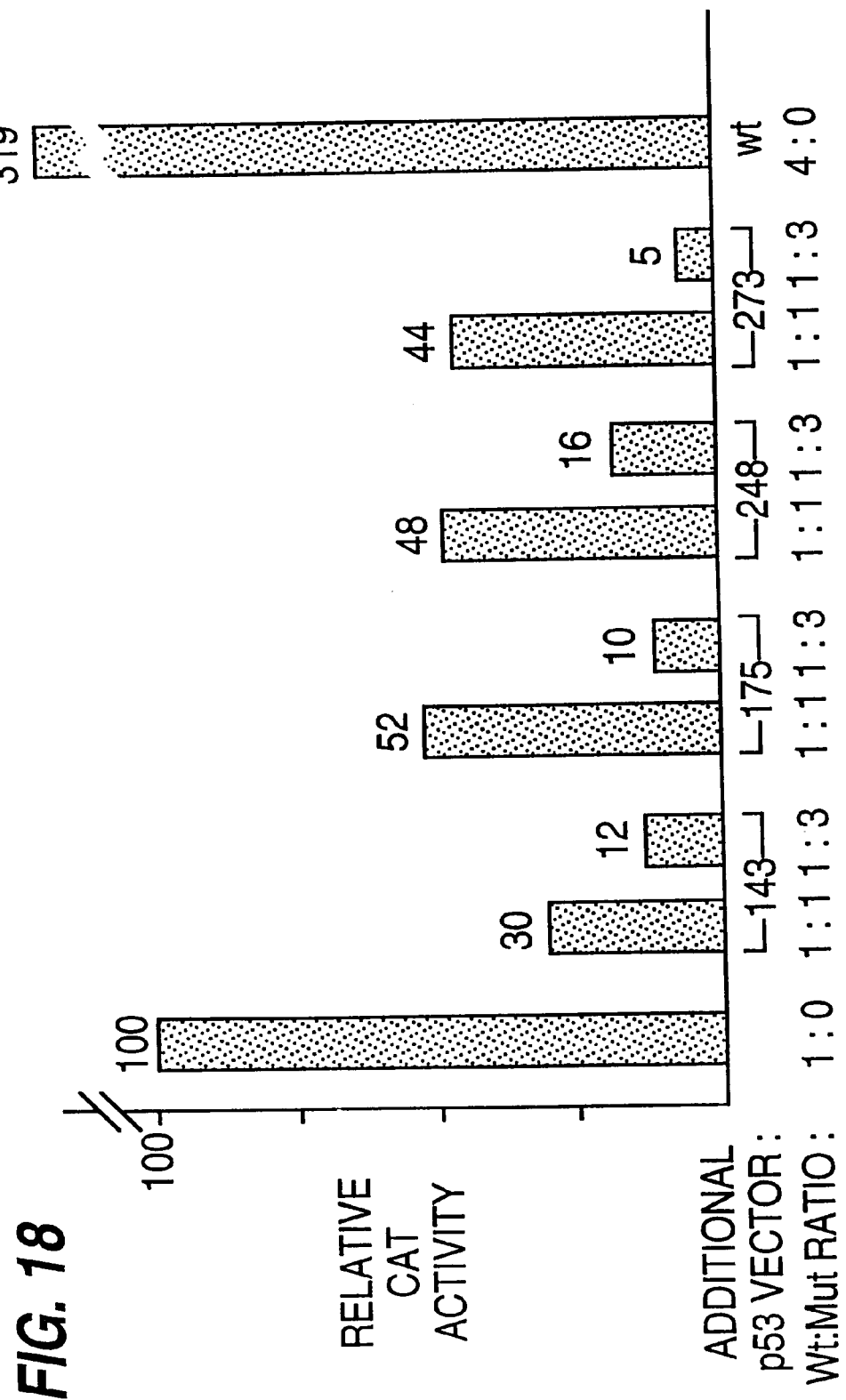
FIG. 18. Dominant-negative effects of various mutant p53 proteins are demonstrated. 0.85 μg of p53-wt was used in all transfections, without or with the addition of 0.85 μg or 2.55 μg mutant p53 construct, or with an additional 2.55 μg p53-wt. 1.7 μg PG$_{13}$-CAT reporter was used in each case. The composite results shown are representative of at least two transfections done on separate days.
Figure 19:
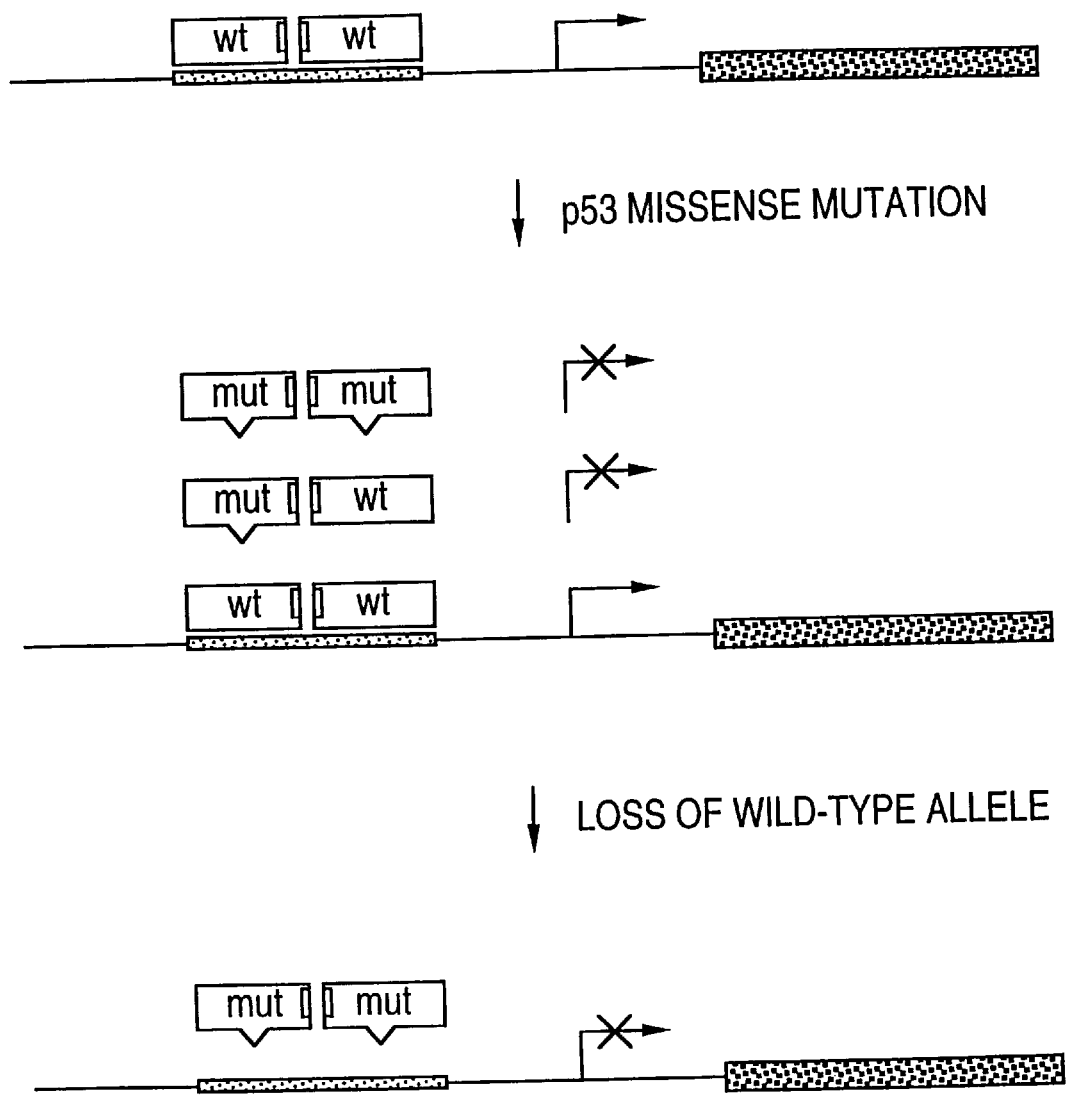
FIG. 19. A biochemical model for the effect of p53 mutations is depicted. Cellular p53 exists as oligomers. Oligomeric p53 binds its recognition sequence of DNA (shaded thick line) and activates the transcription of adjacent genes (filled box). The depiction of p53 dimers is for illustrative purposes only: tetramers and other forms likely occur. Hetero-oligomerization with mutant proteins inactivates the transactivation function of the participating wild-type p53 molecules, producing the dominant-negative effect of missense p53 mutations. The remaining activity provided by the residual wild-type homo-oligomers is lost upon deletion of the remaining wild-type allele, a frequent event in the progression of human neoplasms.

If the transcriptional activation of p53 were fundamental to its biological role, p53 mutants should be able to interfere with this activation, just as p53 mutants can interfere with the tumor-suppressor activity of wild-type p53 when both are expressed (Levine, et al. (1991), *Nature*, 351:453). To assess this possibility, we cotransfected the wild-type and mutant p53 genes with the PG$_{13}$-CAT reporter plasmid into HCT 116 cells (FIGS. 17 and 18). When equal amounts of wild-type and mutant p53 expression vectors were used, the expression of CAT decreased by approximately 50% compared to that achieved by wild-type p53 alone. A three-fold ratio of mutant p53 to wild-type p53 produced an 84–95% reduction. When additional wild-type p53 was substituted for mutant p53 in the cotransfection experiment, the CAT expression increased rather than decreased, as expected (FIG. 18, "wt" lane). Thus, expression of the CAT reporter was dependent on the ratio of wild-type to mutant p53 in the cell.

The dominant-negative effect could be caused by a failure of the mutant/wild-type complexes to bind to DNA or to a failure to activate transcription once bound. To distinguish between these two possibilities, we co-translated wild-type p53 and the 175$^{his}$ mutant of p53 in an experiment similar to that shown in FIG. 14. The mutant p53 protein inhibited the ability of wild-type protein to bind DNA by over 90% when co-expressed at a 3:1 ratio.

We claim:

1. A method for detecting the presence of wild-type p53 protein in a cell, comprising the steps of:
   contacting a p53-specific binding DNA fragment which conforms to the consensus sequence shown in FIG. 10 (SEQ ID NO:3) with a cell lysate from a tissue of a human, to bind the DNA fragment to wild-type p53 present in the cell lysate;
   detecting the presence of wild-type p53 protein in the cell by detecting binding of the DNA fragment to wild-type p53.

2. The method of claim 1 wherein the p53-specific binding DNA fragment comprises nucleotides 103 to 134 as shown in SEQ ID NO:1.

3. The method of claim 1 wherein the p53-specific binding DNA fragment comprises nucleotides 104 to 123 as shown in SEQ ID NO:1.

4. The method of claim 1 wherein the p53-specific binding DNA fragment comprises more than one monomer of the sequence 5'-RRRCWWGYYY-3' (SEQ ID NO:3).

5. The method of claim 4 wherein there are from 0 to 40 nucleotides between said monomers.

6. The method of claim 1 wherein the DNA fragment is labelled with a detectable moiety selected from the group consisting of: a radioactive moiety, a colorimetric moiety, and a fluorescent moiety.

7. The method of claim 1 wherein the step of detecting binding of the DNA fragment to wild-type p53 comprises:
   immunoprecipitating p53 protein with anti-p53 monoclonal antibodies.

8. The method of claim 1 wherein the p53-specific binding DNA fragment comprises more than two monomers of the sequence TGCCT (SEQ ID NO:36).

9. A method of detecting the presence of a wild-type p53 protein in a cell, comprising the steps of:
   providing a tissue section from a human;
   incubating the section with a detectably-labeled p53-specific binding DNA fragment which conforms to the consensus sequence shown in FIG. 10 (SEQ ID NO:3) to bind said DNA fragment to wild-type p53 present in the tissue sample;
   removing unbound DNA fragment from the tissue section; and
   determining the amount of DNA fragment which is bound to the tissue sample.

10. The method of claim 9 wherein the p53-specific binding DNA fragment comprises nucleotides 103 to 134 as shown in SEQ ID NO:1.

11. The method of claim 9 wherein the p53-specific binding DNA fragment comprises nucleotides 104 to 123 as shown in SEQ ID NO:1.

12. The method of claim 9 wherein the p53-specific binding DNA fragment comprises more than one monomer of the sequence 5'-RRRCWWGYYY-3' (SEQ ID NO:3).

13. The method of claim 12 wherein there are between 0 and 40 nucleotides between said monomers.

14. The method of claim 9 wherein the DNA fragment is labelled with a detectable moiety selected from the group consisting of: a radioactive moiety, a colorimetric moiety, and a fluorescent moiety.

15. The method of claim 9 wherein the p53-specific binding DNA fragment comprises more than two monomers of the sequence TGCCT (SEQ ID NO:36).

16. A method of identifying compounds which specifically bind to p53-specific DNA binding sequences, comprising the steps of:
   contacting a p53-specific-binding DNA fragment which conforms to the consensus sequence shown in FIG. 10 (SEQ ID NO:3) with a test compound to bind the test compound to the DNA fragment;
   determining the amount of test compound which is bound to the DNA fragment.

17. The method of claim 16 wherein soluble DNA fragments are incubated with the test compound and the p53-specific-binding DNA fragment immobilized on a solid support, said soluble DNA fragments not having the ability to specifically bind wild-type p53 protein.

18. A method of identifying compounds which specifically bind to p53-specific DNA binding sequences, comprising the steps of:
   contacting a p53-specific-binding DNA fragment which conforms to the consensus sequence shown in FIG. 10 (SEQ ID NO:3), said fragment immobilized on a solid support with both a test compound and wild-type p53 protein to bind the wild-type p53 protein to the DNA fragment;
   determining the amount of wild-type p53 protein which is bound to the DNA fragment, inhibition of binding of wild-type p53 protein by the test compound indicating binding of the test compound to the p53-specific DNA binding sequences.

19. A method for detecting the presence of wild-type p53 protein in a cell, comprising the steps of:
   contacting a p53-specific binding DNA fragment which conforms to the consensus sequence shown in FIG. 10 (SEQ ID NO:3) with a cell lysate from a tissue of a human, to bind the DNA fragment to wild-type p53 present in the cell lysate, wherein said contacting is done under conditions which favor specific binding over non-specific binding;
   detecting the presence of wild-type p53 protein in the cell by detecting binding of the DNA fragment to wild-type p53.

20. The method of claim 19 wherein the steps of contacting is done in the presence of a non-specific competitor of said DNA fragment.

21. A method of detecting the presence of a wild-type p53 protein in a cell, comprising the steps of:
   providing a tissue section from a human;
   incubating the section with a detectably-labeled p53-specific binding DNA fragment which conforms to the consensus sequence shown in FIG. 10 (SEQ ID NO:3)

to bind said DNA fragment to wild-type p53 present in the tissue sample, wherein said incubating is done under conditions which favor specific binding over non-specific binding;

removing unbound DNA fragment from the tissue section; and determining the amount of DNA fragment which is bound to the tissue sample.

22. The method of claim 21 wherein the step of contacting is done in the presence of a non-specific competitor of said DNA fragment.

23. A method of identifying compounds which specifically bind to p53-specific DNA binding sequences, comprising the steps of:

contacting a p53-specific-binding DNA fragment which conforms to the consensus sequence shown in FIG. 10 (SEQ ID NO:3) with a test compound to bind the test compound to the DNA fragment, wherein said contacting is done under conditions which favor specific binding over non-specific binding;

determining the amount of test compound which is bound to the DNA fragment.

24. A method of identifying compounds which specifically bind to p53-specific DNA binding sequences, comprising the steps of:

contacting a p53-specific-binding DNA fragment immobilized on a solid support with both a test compound and wild-type p53 protein to bind the wild-type p53 protein to the DNA fragment which conforms to the consensus sequence shown in FIG. 10 (SEQ ID NO:3), wherein said contacting is done under conditions which favor specific binding over non-specific binding;

determining the amount of wild-type p53 protein which is bound to the DNA fragment, inhibition of binding of wild-type p53 protein by the test compound indicating binding of the test compound to the p53-specific DNA binding sequences.

* * * * *